United States Patent [19]

Kusama et al.

[11] Patent Number: 5,432,267
[45] Date of Patent: Jul. 11, 1995

[54] AMINO SUGAR DERIVATIVES

[75] Inventors: Tsuneo Kusama; Tsunehiko Soga; Akiko Tohgo, all of Tokyo, Japan

[73] Assignee: Daiichi Pharmaceutical Co., Ltd., Tokyo, Japan

[21] Appl. No.: 40,987

[22] Filed: Mar. 31, 1993

[30] Foreign Application Priority Data

Mar. 31, 1992 [JP] Japan .................. 4-074881

[51] Int. Cl.$^6$ ............... C07H 5/04; C07H 11/04; C07H 13/02
[52] U.S. Cl. .................. 536/17.9; 536/55.2; 536/115; 536/116; 536/117; 536/119; 536/120
[58] Field of Search ............ 536/55.2, 115, 116, 536/117, 119, 120, 17.9

[56] References Cited

U.S. PATENT DOCUMENTS 5,278,300 1/1994 Hasegawa et al. ............ 536/55.2

FOREIGN PATENT DOCUMENTS 0330715 9/1989 European Pat. Off. .
0410950A1 1/1991 European Pat. Off. .
8404526 11/1984 WIPO .

OTHER PUBLICATIONS

Proc. Natl. Acad. Sci., vol. 82, issued 1985, Teng et al, "Protection against Gram-Negative Bacteremia and Endotoxemia Wi Human Monoclonal IgM Antibodies", pp. 1790–1794.
Journal of Infectious Diseases, vol. 166, issued 1992, Wortel et al, "Effectiveness of a Human Monoclonal Anti-Endotoxin Antibody (HA-1A) in Gram-Negative Sepsis: Relationship to Endotoxin and Cytokine Levels", pp. 1367–1374.
The New England Journal of Medicine, vol. 324, No. 7, issued 14 Feb. 1991, Ziegler et al, "Treatment of (List continued on next page.)

Primary Examiner—Michael G. Wityshyn
Assistant Examiner—Everett White
Attorney, Agent, or Firm—Sughrue, Mion, Zinn, Macpeak & Seas

[57] ABSTRACT

A compound represented by formula (I):

$$Q^1-Y^1-CO-O-\text{(sugar ring with OR}^2\text{, HO, NHR}^1\text{)}-OCH\begin{smallmatrix}(CH_2)_m-Q^2\\(CH_2)_n-Q^3\end{smallmatrix}$$ (I)

wherein $R^1$ represents $-CO-Z^1-N(Z^{11})-CO-Z^2-H$ or $-CO-Z^3-H$, wherein $Z^1$, $Z^2$, and $Z^3$ each represent an alkylene group having from 1 to 20 carbon atoms, a phenylene group, or a combination thereof, and $Z^{11}$ represents a hydrogen atom, an alkyl group having from 1 to 20 carbon atoms which may be substituted with a phenyl group, a phenyl group which may be substituted with an alkyl group having from 1 to 20 carbon atoms, or an alkylene group having from 1 to 20 carbon atoms which may contain therein a phenylene group; $R^2$ represents $-CO-Z^4-N(Z^{12})-CO-Z^5-H$, $-CO-Z^6-H$ or a hydrogen atom, wherein $Z^4$, $Z^5$, and $Z^6$ each have the same meaning as $Z^1$, and $Z^{12}$ has the same meaning as $Z^{11}$; $Q^1$ and $Q^2$ each represent a carboxyl group or a phosphonoxy group; $Q^3$ represents a hydrogen atom, a carboxyl group or a phosphonoxy group; m represents 0 or an integer of from 1 to 20; n represents 0 or an integer of from 1 to 20; $Y^1$ represents an alkylene group having from 1 to 10 carbon atoms which may contain one or more substituents selected from $-OCOR^{11}$ and $-NHCOR^{12}$, wherein $R^{11}$ represents $-Z^{13}$ or $-Z^7-N(Z^{14})-CO-Z^8-H$ (wherein $Z^7$ and $Z^8$ each have the same meaning as $Z^1$, and $Z^{13}$ and $Z^{14}$ each have the same meaning as $Z^{11}$) and $R^{12}$ represents $-Z^{15}$ or $-Z^9-N(Z^{16})-CO-Z^{10}-H$ (wherein $Z^9$ and $Z^{10}$ each have the same meaning as $Z^1$, and $Z^{15}$ and $Z^{16}$ each have the same meaning as $Z^{11}$), and a salt thereof. The compound inhibits TNF derivation by endotoxin and is therefore useful for the treatment of multiorganic insufficiencies.

8 Claims, No Drawings

OTHER PUBLICATIONS

Gram-Negative Bacteremia and Septic Shock with HA-1A Human Monoclonal Antibody Against Endotoxin-A Randomized, Double-Blind, Placebo-Controlled Trial", pp. 429-436.

JAMA vol. 266, No. 24, issued 25 Dec. 1991, Schulman et al, "Cost-Effectiveness of HA-1A Monoclor Antibody for Gram-Negative Sepsis-Economic Assessment of a New Therapeutic Agent", pp. 3466-3471.

Nature, vol. 330, issued 17 Dec. 1987, Tracey et al, "Anti-Cachectin/TNF Monoclonal Antibodies Prevent Septic Shock during Lethal Bacteraemia" pp. 662-664.

The Lancet, vol. 335, issued 26 May 1990, Exley et al, "Monoclonal Antibody to TNF in Severe Septic Shock", pp. 1275-1277.

Cancer Research, vol. 49, issued 01 Aug. 1989, L. F. Tietze et al "Proton-mediated Liberation of Aldophosphamide from a Nontoxic Prodrug: A Strategy for Tumor-Selective Activation of Cytocidal Drugs" pp. 4179-4184.

Patent Abstracts of Japan, vol. 11, No. 357 (C-458), 20 Nov. 1987.

AMINO SUGAR DERIVATIVES

FIELD OF THE INVENTION

The present invention relates to a novel compound useful as a treating agent for multiorganic insufficiencies. More particularly, it relates to a novel amino sugar derivative which inhibits TNF induction of human macrophage by endotoxin and is therefore used in the treatment of multiorganic insufficiencies.

BACKGROUND OF THE INVENTION

Acute pulmonary lesions or multiorganic insufficiencies are diseases of extremely high death ratio, and intensive studies have been given to these diseases in terms of pathology, early diagnosis and treatment. The onset of these diseases often follows or accompany infectious diseases. In such cases, endotoxin is considered to play a major role. Endotoxin is known to activate phagocytes, such as macrophage, and various cytokines which are derived through the activation are considered to participate in the symptoms.

Cytokines deeply concerned with pulmonary lesions or multiorganic insufficiencies include TNF (tumor necrosis factor), interleukins, etc. These cytokines have been confirmed to induce an acute pulmonary lesion in animal experiments.

Studies have now been directed to monoclonal antibodies against endotoxin or TNF as promising prophylactic or treating agents for the above-mentioned diseases. While their effectiveness in animal models has been ascertained, a sufficient clinical treatment has not yet been established.

SUMMARY OF THE INVENTION

As a result of extensive searches for a compound which can be clinically applied to produce excellent efficacy in the treatment of the above-mentioned diseases, the inventors have found that a compound represented by formula (I) shown below meets the purpose of inhibiting TNF derivation of human macrophage by endotoxin and thus completed the present invention.

The present invention relates to a compound represented by formula (I):

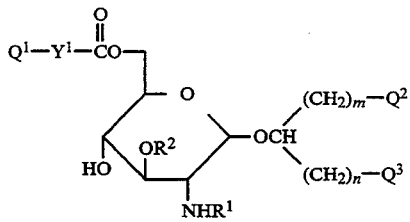

wherein $R^1$ represents $-CO-Z^1-N(Z^{11})-CO-Z^2-H$ or $-CO-Z^3-H$, wherein $Z^1$, $Z^2$, and $Z^3$ each represent an alkylene group having from 1 to 20 carbon atoms, a phenylene group, or a combination thereof, and $Z^{11}$ represents a hydrogen atom, an alkyl group having from 1 to 20 carbon atoms which may be substituted with a phenyl group, a phenyl group which may be substituted with an alkyl group having from 1 to 20 carbon atoms, or an alkylene group having from 1 to 20 carbon atoms which may contain therein a phenylene group; $R^2$ represents $-CO-Z^4-N(Z^{12})-CO-Z^5-H$, $-CO-Z^6-H$ or a hydrogen atom, wherein $Z^4$, $Z^5$, and $Z^6$ each have the same meaning as $Z^1$, and $Z^{12}$ has the same meaning as $Z^{11}$; $Q^1$ and $Q^2$ each represent a carboxyl group or a phosphonoxy group; $Q^3$ represents a hydrogen atom, a carboxyl group or a phosphonoxy group; m represents 0 or an integer of from 1 to 20; n represents 0 or an integer of from 1 to 20; $Y^1$ represents an alkylene group having from 1 to 10 carbon atoms which may contain one or more substituents selected from $-OCOR^{11}$ and $-NHCOR^{12}$, wherein $R^{11}$ represents $-Z^{13}$ or $-Z^7-N(Z^{14})-CO-Z^8-H$ (wherein $Z^7$ and $Z^8$ each have the same meaning as $Z^1$, and $Z^{13}$ and $Z^{14}$ each have the same meaning as $Z^{11}$) and $R^{12}$ represents $-Z^{15}$ or $-Z^9-N(Z^{16})-CO-Z^{10}-H$ (wherein $Z^9$ and $Z^{10}$ each have the same meaning as $Z^1$, and $Z^{15}$ and $Z^{16}$ each have the same meaning as $Z^{11}$), and a salt thereof.

DETAILED DESCRIPTION OF THE INVENTION

In formula (I), specific examples of the groups represented by $R^1$ are tetradecanoyl, dodecanoyl, decanoyl, N-dodecanoylglycyl, N-dodecanoylsarcosyl, 6-octanoylaminohexanoyl, 8-hexanoylaminooctanoyl, 6-benzoylaminohexanoyl, 8-benzoylaminooctanoyl, p-octanoylaminobenzoyl, 8-phenyloctanoyl, p-octylbenzoyl, and N-dodecanoyl-N-dodecylglycyl groups. Further, it is particularly preferable that the total carbon atoms of $Z^1$ and $Z^2$ are 10 to 16 and that $Z^3$ is an acyl group having from 10 to 16 carbon atoms.

Specific examples of the groups represented by $R^2$ are a hydrogen atom and tetradecanoyl, dodecanoyl, decanoyl, N-dodecanoylglycyl, N-dodecanoylsarcosyl, 6-octanoylaminohexanoyl, 8-hexanoylaminooctanoyl, 6-benzoylaminohexanoyl, 8-benzoylaminooctanoyl, p-octanoylaminobenzoyl, 8-phenyloctanoyl, p-octylbenzoyl, and N-dodecanoyl-N-dodecylglycyl groups. Further, it is particularly preferable that the total carbon atoms of $Z^4$ and $Z^5$ are 10 to 16 and that $Z^6$ is an acyl group having from 10 to 16 carbon atoms.

Specific examples of the groups represented by $Z^1$, $Z^2$, $Z^3$, $Z^4$, $Z^5$, $Z^6$, $Z^7$, $Z^8$, $Z^9$ and $Z^{10}$ are phenylene ($-C_6H_4-$), methylene ($-CH_2-$), ethylene ($-CH_2CH_2-$), tetramethylene ($-(CH_2)_4-$), pentamethylene ($-(CH_2)_5-$), hexamethylene ($-(CH_2)_6-$), heptamethylene ($-(CH_2)_7-$), nonamethylene ($-(CH_2)_9-$), undecamethylene ($-(CH_2)_{11}-$), dodecamethylene ($-(CH_2)_{12}-$) and tridecamethylene ($-(CH_2)_{13}-$) groups, and groups of formulae $-CH_2C_6H_4-$, $-(CH_2)_7C_6H_4-$, and $-CH_2C_6H_4CH_2-$.

Specific examples of the groups represented by $Z^{11}$, $Z^{12}$, $Z^{13}$, $Z^{14}$, $Z^{15}$, and $Z^{16}$ include phenyl-substituted or unsubstituted alkyl groups, e.g., methyl, ethyl, pentyl, heptyl, nonyl, undecyl, dodecyl, tridecyl, benzyl, 3-phenylpropyl, 5-phenylpentyl, and 7-phenylheptyl groups; alkyl-substituted or unsubstituted phenyl groups, e.g., p-hexylphenyl, p-octylphenyl, and p-decylphenyl groups; phenylene-containing or not containing alkylene groups, e.g., 7-(p-toluyl)heptyl and 3-(p-butylphenyl)propyl groups; and a hydrogen atom.

Specific examples of the group $-OCOR^{11}$ are decanoyloxy, dodecanoyloxy, tetradecanoyloxy, 8-phenyloctanoyloxy, 6-benzoylaminohexanoyloxy, N-dodecanoylglycyloxy, N-dodecanoylsarcosyloxy, 6-octanoylaminohexanoyloxy, 8-hexanoylaminooctanoyloxy, 6-benzoylaminohexanoyloxy, 8-benzoylaminooctanoyloxy, p-octanoylaminobenzoyloxy, 8-phenyloctanoyloxy, p-octylbenzoyloxy, and N-dodecanoyl-N-dodecylglycyloxy groups. Further, it is particularly preferable that the totals-carbon atoms of the group —OCOR[11] except for $Z^{14}$ are 10 to 16.

Specific examples of the group —NHCOR[12] are dodecanoylamino, tetradecanoylamino, N-dodecanoylglycylamino, N-dodecanoylsarcosylamino, 6-octanoylaminohexanoylamino, 8-hexanoylaminooctanoylamino, 6-benzoylaminohexanoylamino, 8-benzoylaminooctanoylamino, p-octanoylaminobenzoylamino, 8-phenyloctanoylamino, p-octylbenzoylamino, and N-dodecanoyl-N-dodecylglycyl-dodecanoylamino groups. Further, it is particularly preferable that the total carbon atoms of the group —NHCOR[12] except for $Z^{16}$ are 10 to 16.

Where $Y^1$ contains two or more substituents selected from —OCOR[11] and —NHCOR[12], the moieties represented by $R^{11}$ or $R^{12}$ may be not be the same and may be an arbitrarily selected combination, for example, a combination of tetradecane and dodecane groups, a combination of tetradecane and dodecanoylaminomethyl groups, a combination of tetradecane, dodecane, and decane groups, and a combination of two tetradecane groups and one dodecane group. Further, it is particularly preferable that $Y^1$ is an ethylene or propylene group which contains one or two substituents selected from —OCOR[11] and —NHCOR[12].

The compounds according to the present invention will be illustrated in more detail by way of specific examples of various substituent groups and their combinations. In the following illustration, complicated groups are represented by symbols or abbreviations as shown below. Groups other than those specifically illustrated below may also be expressed by using such symbols or abbreviations in combination.

Symbols or Abbreviations

—C14: Tetradecanoyl (—CO(CH$_2$)$_{12}$CH$_3$)

—GlyC12: N-Dodecanoylglycyl (—COCH$_2$NHCOCH(CH$_2$)$_{10}$CH$_3$)

—COCH(NHC14)CH$_2$CH$_2$COOH: 4-Carboxy-2-(tetradecanoylamino)butanoyl (—COCH(NHCO(CH$_2$)$_{12}$CH$_3$)CH$_2$CH$_2$COOH)

—COCH(NHC14)CH$_2$OPO(OH)$_2$: 3-Phosphonoxy-2-tetradecanoylamino (—COCH(NHCO(CH$_2$)$_{12}$CH$_3$)CH$_2$OPO(OH)$_2$)

—C8NBz: 8-Benzoylaminooctanoyl (—CO(CH$_2$)$_7$NHCOC$_6$H$_5$)

—BzNC8: p-Octanoylaminobenzoyl (—COC$_6$H$_4$NHCO(CH$_2$)$_6$CH$_3$)

—C6NC8: 6-Octanoylaminohexanoyl (—CO(CH$_2$)$_5$NHCO(CH$_2$)$_6$CH$_3$)

—C6NBz: 6-Benzoylaminohexanoyl (—CO(CH$_2$)$_5$NHCOC$_6$H$_5$)

—SarC12: N-Dodecanoylsarcosyl (—COCH$_2$N(CH$_3$)CO(CH$_2$)$_{10}$CH$_3$)

| Examples of Groups: | |
|---|---|
| —CO—Y$^1$—Q$^1$: | —COCH$_2$CH$_2$CH(NHC14)COOH, |
| | —COCH$_2$CH(OC14)COOH, |
| | —COCH$_2$CH(OC8NBz)COOH, |
| | —COCH(OC8NBz)CH(OC8NBz)COOH, |
| | —COCH$_2$CH(NHC8NBz)CH$_2$COOH, |
| | —COCH(NHSarC12)CH$_2$CH$_2$COOH, |
| | —COCH(NHC14)CH$_2$CH$_2$COOH, |
| | —COCH(NHC14)CH$_2$COOH, |
| | —COCH(NHC6NBz)CH$_2$CH$_2$COOH, |
| | —COCH(NHC8C$_6$H$_5$)CH$_2$CH$_2$COOH, |
| | —COCH(NHBzNC8)CH$_2$CH$_2$COOH, |
| | —COCH(NHC8NBz)CH$_2$COOH, |
| | —COCH(NHC8NBz)CH$_2$CH$_2$COOH, |
| | —COCH(NHC8NBz)CH(OGlyC12)COOH, and |
| | —COCH(NHC14)CH(OC14)COOH |
| R$^1$ or R$^2$: | —C14, —C12, —GlyC12, —BzNC8, —C6NC8, —SarC12, and —C6NBz |
| Q$^2$ or Q$^3$: | —OPO(OH)$_2$, —COOH, and H |

TABLE 1

Examples of Combinations of Groups in Formula (I):

| Compound No. | —CO—Y$^1$—Q$^1$ | Other Substituent (see Table 2) |
|---|---|---|
| 1 | —COCH((R)—OC14)CH((R)—OC14)COOH | type 1 |
| 2 | —COCH((R)—NHC14)CH$_2$CH$_2$COOH | type 1 |
| 3 | —COCH((R)—NHC14)CH$_2$OPO(OH)$_2$ | type 1 |
| 4 | —COCH((R)—NHC8NBz)CH$_2$CH$_2$COOH | type 1 |
| 5 | —COCH((R)—NHC14)CH$_2$CH$_2$COOH | type 2 |
| 6 | —COCH((R)—NHC8NBz)CH$_2$CH$_2$COOH | type 3 |
| 7 | —COCH((R)—NHC6NBz)CH$_2$CH$_2$COOH | type 3 |
| 8 | —COCH((R)—NHC14)CH$_2$CH$_2$COOH | type 4 |
| 9 | —COCH((S)—NHC14)CH$_2$CH$_2$COOH | type 3 |
| 10 | —COCH((R)—OC14)CH((R)—OC14)COOH | type 5 |
| 11 | —COCH((R)—NHC14)CH$_2$CH$_2$COOH | type 6 |
| 12 | —COCH((R)—NHC14)CH$_2$CH$_2$COOH | type 3 |
| 13 | —COCH((R)—NHBzNC8)CH$_2$CH$_2$COOH | type 3 |
| 14 | —COCH((R)—NHCOCH$_2$C$_6$H$_4$NHC8)CH$_2$CH$_2$COOH | type 3 |
| 15 | —COCH((R)—NHC14)CH$_2$CH$_2$COOH | type 3 |
| 16 | —COCH((R)—NHCOCH$_2$N(C12)(CH$_2$)$_{11}$CH$_3$)CH$_2$CH$_2$COOH | type 4 |
| 17 | —COCH((R)—NHC8C$_6$H$_5$)CH$_2$CH$_2$COOH | type 3 |
| 18 | —COCH$_2$CH((R)—NHBz(CH$_2$)$_7$CH$_3$)COOH | type 3 |
| 19 | —COCH$_2$CH((S)—NHC14)COOH | type 3 |
| 20 | —COCH$_2$CH((S)—OC14)COOH | type 3 |
| 21 | —COCH((S)—NHC14)Ch$_2$COOH | type 3 |
| 22 | —COCH((R)—NHC14)CH$_2$COOH | type 3 |
| 23 | —COCH((R)—NHC6—C$_6$H$_4$—C$_2$H$_5$)CH$_2$CH$_2$COOH | type 3 |

TABLE 2

| | Substituents Other than —CO—Y$^1$—Q$^1$ | | | | | |
|---|---|---|---|---|---|---|
| Type | R$^1$ | R$^2$ | Q$^2$ | Q$^3$ | m | n |
| 1 | —C14 | —GlyC12 | —COOH | —COOH | 1 | 1 |
| 2 | —C14 | —C14 | —OPO(OH)$_2$ | —H | 1 | 0 |
| 3 | —C14 | —C14 | —COOH | —COOH | 1 | 1 |
| 4 | —C8NBz | —C14 | —COOH | —COOH | 1 | 1 |
| 5 | —C14 | —H | —COOH | —COOH | 1 | 1 |
| 6 | —C14 | —C8NBz | —COOH | —COOH | 1 | 1 |

The salts of the compound of formula (I) include salts with an alkali metal, e.g., sodium and potassium, an alkaline earth metal, e.g., calcium and magnesium, ammonia, an organic amine, e.g., triethylamine, pyridine, N-methylglucamine and tris(hydroxymethyl)aminomethane, etc.

The compounds of the present invention can be prepared according to the following reaction formula:

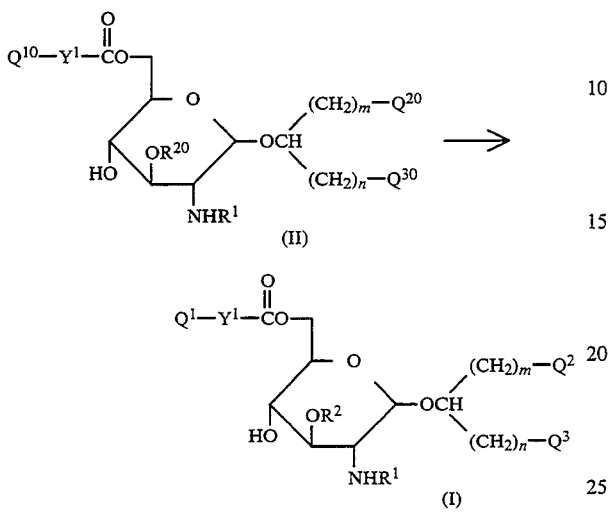

wherein $Q^{10}$ and $Q^{20}$ each represent a protected carboxyl group or a protected phosphonoxy group; $Q^{30}$ represents a protected carboxyl group, a protected phosphonoxy group or a hydrogen atom; $R^{20}$ represents a hydroxyl-protective group, $-CO-Z^4-N(Z^{1-2})-CO-Z^5-H$ or $-CO-Z^6-H$; and $Y^1$, $Z^4$, $Z^5$, $Z^6$, and $Z^{12}$ are as defined above.

Protective groups for a carboxyl group include a benzyl group, etc., which may be substituted with a halogen atom, a nitro group, a lower alkoxy group, etc.

Protective groups for a phosphonoxy group include a phenyl group, a benzyl group, etc., each of which may be substituted with a halogen atom, a nitro group, a lower alkoxy group, etc.

Protective groups for a hydroxyl group include a benzyl group, a benzyloxycarbonyl group, etc., each of which may be substituted with a halogen atom, a nitro group, a lower alkoxy group, etc.; and a trichloroethoxycarbonyl group.

The compound of formula (I) can be prepared by releasing the protective groups of the carboxyl and/or phosphonoxy groups and, if any, the protective group of the hydroxyl group. Removal of these protective groups may suitably be carried out by catalytic reduction of the compound of formula (II) in a solvent, such as tetrahydrofuran, methanol, ethanol, acetic acid or water, or a mixture thereof, in a hydrogen atmosphere in the presence of a catalyst, such as palladium black, palladium-on-carbon, and platinum dioxide.

Where the compound of formula (II) carries a trichloroethoxycarbonyl group as a hydroxyl-protective group and other protective groups, the reaction is generally conducted first by releasing the trichloroethoxycarbonyl group by treating with zinc powder in acetic acid and then releasing the other protective groups.

If desired, the resulting compound is purified by, for example, column chromatography on silica gel and then subjected to desalting by electric dialysis, acid precipitation, a treatment with an ion exchange resin, etc.

The compound of the present invention may be produced in the form of its salt by an appropriate method, for example, addition of a requisite amount of a base followed by precipitation or lyophilization.

While the compound of the present invention embraces a compound having an α-configuration and that having a β-configuration at the 1-position of the sugar moiety, the compound having an α-configuration exhibits superior effects in many cases.

The starting compound of formula (II) may be prepared through route A or B shown below.

Route A:

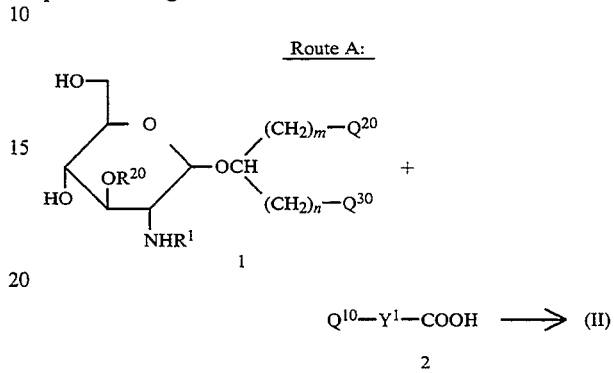

The compound of formula (II) can be prepared by ester condensation between the primary hydroxyl group at the 6-position of compound 1 and the carboxyl group of compound 2 by an acid chloride method or a carbodiimide method, etc. In a carbodiimide method using a condensing agent, such as dicyclohexylcarbodiimide, the reaction may be accelerated by additionally using a catalyst, e.g., 4-dimethylaminopyridine, or an active ester-forming reagent, e.g., 1-hydroxybenzotriazole.

Route B

The compound of formula (II) wherein $Y^1$ carries a moiety represented by $-NHCOR^{12}$ may also be prepared as follows.

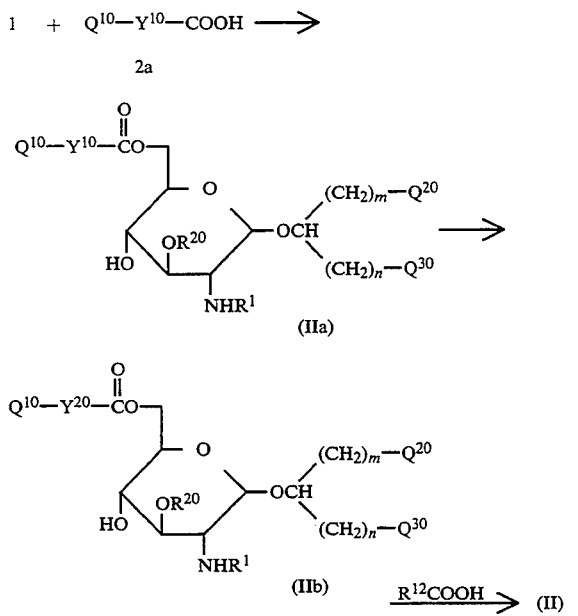

wherein $Y^{10}$ represents an alkylene group which contains at least one protected amino group and which may further contain one or more substituents selected from —OCOR[11] and —NHCOR[12]; Y[20] represents the same group as Y[10], except for the protective group of the protected amino group present in Y[10] has been removed; and R[11] and R[12] are as defined above.

Compound 2a having a protected amino group is condensed with compound 1 in the same manner as in Route A. The amino-protective group of the resulting compound (IIa) is released by, for example, treating with trifluoroacetic acid or with zinc powder in acetic acid. The resulting compound (IIb) is then reacted with a carboxylic acid R[12]COOH according to an acid chloride method, a carbodiimide method, an Eintopf method, an active ester method, etc. to obtain the compound of formula (II) having —NHCOR[12].

The amino protective groups include those commonly employed in the art, e.g., a t-butoxycarbonyl group, a trichloroethoxycarbonyl group, and a methoxybenzyloxycarbonyl group.

The starting compound 1 can be synthesized in accordance with processes reported in literature (e.g., T. Kusama et al., Chem. Pharm. Bull., Vol. 38, p. 3366 (1990) and ibid, Vol. 39, p. 3244 (1991)) or analogous processes.

The starting compound 2 or 2a can easily be synthesized from carboxylic acid derivatives having an amino group and/or a hydroxyl group and/or a carboxyl group, e.g., tartaric acid, glutamic acid, and serine. For example, an amino-protective group, e.g., a t-butoxycarbonyl group or a 2,2,2-trichloroethoxycarbonyl group, or an acyl group represented by R[12]CO— can be introduced to an amino-containing compound, or an acyl group represented by R[11]CO— or a protected phosphonoxy group can be introduced to a hydroxyl-containing compound. When starting with a compound having two carboxyl groups, a desired compound may be obtained by protecting one of them with a benzyl group or a like protective group.

Some of the starting compounds used in the above-mentioned synthesis are commercially available. The synthesis of the starting compounds is illustrated in Reference Examples described below.

The compounds according to the present invention exhibit an excellent activity which inhibits TNF derivation by endotoxin. Therefore, the compounds of the present invention are useful for treatment and prophylaxis of multiorganic insufficiencies.

The compounds of the present invention can be administered orally or parenterally by, for example, injection.

For intravenous injection, the compound of the present invention may be used at a dosage of 0.1 to 30 mg in adult human per day, though more less varying depending on the purpose of administration (therapeutic use or preventive use, etc.), and the symptoms.

The compound of the invention can be formulated into various pharmaceutical preparations with excipients, such as stabilizers and isotonizing agents. The preparations can be prepared by the conventional techniques known in the art.

The present invention will now be illustrated in greater detail with reference to Examples, but it should be understood that the present invention is not construed as being limited thereof. All the percents are by weight unless otherwise indicated.

REFERENCE EXAMPLE 1

Preparation of Monobenzyl 2,3-Bis-O-tetradecanoyl-L-tartrate

In 20 ml of ethyl acetate was dissolved 1.48 g of monobenzyl L-tartrate, and 1.35 g of phenacyl bromide and 0.94 ml of triethylamine were added to the solution at room temperature, followed by stirring at that temperature for 24 hours. The reaction mixture was washed successively with water, 1N hydrochloric acid, 5% sodium hydrogen-carbonate aqueous solution, and a saturated sodium chloride aqueous solution, and dried over anhydrous sodium sulfate. The solvent was removed by distillation under reduced pressure, and the residue was purified by column chromatography on silica gel (eluent: chloroform:acetone=19:1, changed en route to 9:1) to obtain 2.10 g of benzylphenacyl L-tartrate as a pale yellow oily substance.

$[\alpha]_D^{25}$: +1.3° (c=1.2, chloroform) $^1$H-NMR (CDCl$_3$/TMS) δ: 3.0 (2H, br), 4.81 (2H, m), 5.30 (2H, s), 5.49 (2H, s), 7.2–8.0 (10H, m)

In 30 ml of dried methylene chloride was dissolved 2.01 g of the resulting benzylphenacyl L-tartrate, and 3.33 g of tetradecanoyl chloride, 1.09 ml of pyridine, and 0.14 g of 4-dimethylaminopyridine were added thereto under ice-cooling, followed by stirring at the same temperature for 1 hour. The reaction mixture was washed successively with water, 1N hydrochloric acid, and a saturated sodium chloride aqueous solution and dried over anhydrous sodium sulfate. The solvent was removed by distillation under reduced pressure, and the residue was purified by column chromatography on silica gel (eluent: hexane:ethyl acetate=9:1, changed en route to 4:1) to obtain 3.81 g of benzylphenacyl 2,3-bis-O-tetradecanoyl-L-tartrate as a white waxy solid.

Melting Point: 51°–52° C. $[\alpha]_D^{25}$: +12.0° (C=2.5, chloroform) IR (KBr) $\nu_{max}$: 1770, 1750, 1705, 1210, 1150 cm$^{-1}$ $^1$H-NMR (CDCl$_3$/TMS) δ: 0.88 (6H, s-t), 1.25 (40H, s), 2.1–2.7 (4H, m), 5.19 (1H, AB type d, J=16Hz), 5.21 (2H, s-ABq), 5.57 (1H, AB type d, J=16Hz), 5.87 (1H, d, J=3Hz), 5.93 (1H, d, J=3Hz), 7.3–7.9 (10H, m)

In 40 ml of acetic acid was dissolved 3.404 g of the resulting compound, and 2.0 g of zinc powder was added thereto, followed by vigorously stirring at room temperature. Two hours later, the mixture was heated to 50° C. and stirred for 3 hours while adding three 1 g portions of zinc powder. The insoluble matter was removed by filtration, and the filtrate was washed with chloroform and distilled under reduced pressure to remove the solvent. Toluene was added to the residue and then removed by distillation under reduced pressure. Toluene addition and removal were repeated, and the residue was diluted with chloroform, washed with 1N hydrochloric acid, and dried over anhydrous sodium sulfate. The solvent was removed by distillation under reduced pressure, and the residue was purified by silica gel column chromatography (eluent: chloroform containing methanol in a concentration of 2%, changed en route to 10%) to obtain 2.88 g of monobenzyl 2,3-bis-O-tetradecanoyl-L-tartrate as a colorless oily substance.

$[\alpha]_D^{25}$: +9.8° (C=1.9, chloroform) $^1$H-NMR (CDCl$_3$/TMS) δ: 0.88 (6H, t, J=7Hz), 1.25 (40H, s), 1.4–1.6 (4H, m), 2.1–2.4 (4H, m), 5.07 (1H, AB type d, J=12Hz), 5.18 (1H, AB type d, J=13Hz), 5.59 (1H, br), 5.92 (1H, br), 7.27 (5H, m)

REFERENCE EXAMPLE 2

Preparation of
N-t-Butoxycarbonyl-O-diphenylphosphono-D-serine

In 30 ml of dried methylene chloride was dissolved 3.75 g of benzyl N-t-butoxycarbonyl-D-serine, and 1.23 ml of pyridine, 1.86 g of 4-dimethylaminopyridine, and 4.09 g of diphenyl phosphorochloridate were successively added thereto at room temperature, followed by stirring at that temperature for 3 hours. The reaction mixture was washed successively with 1N hydrochloric acid and a saturated sodium chloride aqueous solution. The organic layer was dried over anhydrous sodium sulfate, and the solvent was removed by distillation under reduced pressure. The residue was purified by column chromatography on silica gel (eluent: 2% acetone-containing chloroform) to obtain 5.38 g of benzyl N-t-butoxycarbonyl-O-diphenylphosphono-D-serine as a white solid.

Melting point: 108°–109° C. $[\alpha]_D^{25}$: −14.8° (C=1.2, chloroform) IR (KBr) $\nu_{max}$: 3300, 1750, 1710, 1590, 1530, 1490 cm$^{-1}$ $^1$H-NMR (CDCl$_3$/TMS) δ: 1.42 (9H, s), 4.5–4.7 (3H, m), 5.07 (1H, AB type d, J=12Hz), 5.16 (1H, AB type d, J=12Hz), 5.39 (1H, d, J=8Hz), 7.1–7.4 (15H, m)

In 40 ml of tetrahydrofuran was dissolved 5.19 g of the resulting compound, and 200 mg of 10% palladium-on-carbon was added thereto, followed by vigorously stirring at room temperature in a hydrogen stream for 2 hours. The catalyst was removed by filtration, and the solvent was removed from the filtrate by distillation under reduced pressure. The residue was dissolved in ethyl acetate and extracted with a 5% sodium hydrogencarbonate aqueous solution. The aqueous layer was adjusted to pH 2 to 3 with a citric acid aqueous solution and extracted with ethyl acetate. The extract was washed with a saturated sodium chloride aqueous solution. The organic layer was dried over anhydrous sodium sulfate, and the solvent was removed by distillation under reduced pressure to obtain 4.11 g of the titled compound as a colorless oily substance.

$[\alpha]_D^{25}$: −32.3° (C=1.2, chloroform) $^1$H-NMR (CDCl$_3$/TMS) δ: 1.42 (9H, s), 4.56 (2H, m), 4.67 (1H, m), 5.54 (1H, d, J=7Hz), 7.15–7.4 (10H, m)

REFERENCE EXAMPLE 3

Preparation of α-Benzyl N-Tetradecanoyl-L-aspartate

In 20 ml of water was suspended 447 mg of α-benzyl L-aspartate, and 1.34 g of sodium hydrogencarbonate was dissolved therein. To the suspension was added 1.09 ml of tetradecanoyl chloride under ice-cooling and, after warming to room temperature, the mixture was stirred for 4 hours. To the reaction mixture was further added 0.81 ml of tetradecanoyl chloride, followed by stirring at room temperature for 10 hours. The reaction mixture was rendered acidic with hydrochloric acid and extracted with ethyl acetate. The extract was dried over anhydrous sodium sulfate, and the solvent was removed by distillation under reduced pressure. The residue was purified by silica gel column chromatography (developing solvent: 2% methanol-containing chloroform). Recrystallization from a mixed solvent of diethyl ether and hexane yielded 432 g of the titled compound.

Melting Point: 78°–80° C. $[\alpha]_D^{25}$: +23.6° (c=0.6, chloroform) $^1$H-NMR (CDCl$_3$/TMS) δ: 0.88 (3H, t, J=7Hz), 1.24 (20H, s), 1.59 (2H, m), 2.22 (2H, t, J=7Hz), 2.85 (1H, dd, J=7Hz, 4Hz), 3.07 (1H, dd, J=7Hz, 4Hz), 4.92 (1H, m), 5.17 (1H, d, J=12Hz), 5.20 (1H, d, J=13Hz), 6.62 (1H, d, J=8Hz), 7.3–7.37 (5H, m)

REFERENCE EXAMPLE 4

Preparation of α-Benzyl O-Tetradecanoyl-L-malate

α-Benzyl L-malate was converted to a benzylphenacyl ester, which was then reacted with tetradecanoyl chloride, and finally the phenacyl group was removed in the same manner as in Reference Example 1 to obtain the titled compound as a colorless oily substance.

$[\alpha]_D^{25}$: −16.5° (C=1.0, chloroform) $^1$H-NMR (CDCl$_3$/TMS) δ: 0.88 (3H, t, J=7Hz), 1.25 (20H, m), 1.60 (2H, m), 2.36 (2H, m), 2.92 (2H, d, J=6Hz), 5.16 and 5.21 (each 1H, AB type d, J=12Hz), 5.52 (1H, t, J=6Hz), 7.3–7.4 (5H, m)

REFERENCE EXAMPLE 5

Preparation of
2-Benzyloxycarbonyl-1-(benzyloxy-carbonylmethyl)ethyl
6-O-[3-Benzyloxycarbonyl-2R,3R-bis(tetradecanoyloxy)propanoyl]-2-deoxy-3-O-(N-dodecanoylglycyl)-2-tetradecanoylamino-α-D-glucopyranoside In 5 ml of dried methylene chloride was dissolved 308 mg of 2-benzyloxycarbonyl-1-(benzyloxycarbonylmethyl)ethyl 2-deoxy-3-O-(N-dodecanoylglycyl)-2-tetradecanoyl-amino-α-D-glucopyranoside, and 238 mg of monobenzyl 2,3-bis-O-tetradecanoyl-L-tartrate and 4 mg of 4-dimethylaminopyridine were added to the solution. The mixture was once cooled with ice, and 81 mg of dicyclohexylcarbodiimide and 50 mg of 1-hydroxybenzotriazole were added thereto, followed by stirring at room temperature for 3 hours. To the reaction mixture was added 1 ml of methanol, followed by stirring, and the mixture was diluted with chloroform, washed successively with 1N hydrochloric acid, a 5% sodium hydrogencarbonate aqueous solution, and a saturated sodium chloride aqueous solution, and dried over anhydrous sodium sulfate. The solvent was removed by distillation under reduced pressure, and the residue was purified by column chromatography on silica gel (eluent: 5% acetone-containing chloroform, changed en route to 1% methanol-containing chloroform) to obtain 294 mg of the titled compound as a colorless oily substance.

$[\alpha]_D^{25}$: +26.2° (c=1.4, chloroform) $^1$H-NMR (CDCl$_3$TMS) δ: 0.88 (12H, t, J=6Hz), 1.25 (76H, m), 1.5–1.7 (8H, m), 2.1–2.4 (8H, m), 2.60 (1H, dd, J=16Hz, 7Hz), 2.68 (2H, m), 2.84 (1H, dd, J=16Hz, 6Hz), 3.55 (1H, t, J=10Hz), 3.85 (1H, dd, J=18Hz, 5Hz), 3.88 (1H, m), 4.10 (1H, dd, J=17Hz, 6Hz), 4.20 (1H, td, J=10Hz, 4Hz), 4.4 (3H, m), 4.88 (1H, d, J=4Hz), 5.00 (1H, t, J=10Hz), 5.05–5.25 (6H, m), 573 and 5.80 (each 1H, d, J=3Hz), 6.40 (1H, t, J=5Hz), 6.61 (1H, d, J=9Hz), 7.33 (15H, m)

REFERENCE EXAMPLE 6

Preparation of
2-Benzyloxycarbonyl-1-(benzyloxycarbonylmethyl)ethyl
6-O-[4-Benzyloxycarbonyl-2R-(tetradecanoylamino)-butanoyl]-2-deoxy-3-O-(N-dodecanoylglycyl)-2-tetradecanoylamino-α-D-glucopyranoside In 6 ml of dried methylene chloride was dissolved 380 mg of 2-benzyloxycarbonyl-1-(benzyloxycarbonylmethyl)ethyl 2-deoxy-3-O-(N-dodecanoylglycyl)-2-tetradecanoyl-amino-α-D-glucopyranoside, and 143 mg of γ-benzyl N-t-butoxycarbonyl-D-glutamate and 5 mg of 4-dimethylaminopyridine were added to the solution. After cooling with ice, 100 mg of dicyclohexylcarbodiimide was added thereto, followed by stirring at the same temperature for 45 minutes. To the reaction mixture was added 1 ml of methanol, followed by stirring, and the solvent was removed by distillation under reduced pressure. The residue was purified by column chromatography on silica gel (eluent: 5% acetone-containing chloroform, changed en route to 2% methanol-containing chloroform) to obtain 334 mg of a yellow oily substance.

The oily substance (320 mg) was dissolved in 4 ml of dried methylene chloride, and 4 ml of trifluoroacetic acid was added thereto while cooling with ice, followed by stirring at the same temperature for 1 hour. The solvent was removed by distillation under reduced pressure. To the residue was added toluene, followed by distillation under reduced pressure. Toluene addition and solvent removal by distillation were repeated to obtain an oily substance.

Separately, 86 mg of myristic acid and 61 mg of 1-hydroxybenzotriazole were dissolved in 3 ml of dried tetrahydrofuran, and 83 mg of dicyclohexylcarbodiimide was added to the solution under ice-cooling. After warming to room temperature, the mixture was stirred for 2 hours, and the precipitated crystal was removed by filtration. The filtrate was combined with a solution of the above-prepared oily substance in 6 ml of dried methylene chloride while cooling with ice, and 52 μl of triethylamine was added thereto, followed by stirring at room temperature for 17 hours. The solvent was removed by distillation under reduced pressure. The residue was purified by column chromatography on silica gel (eluent: 5% acetone-containing chloroform, changed en route to 1% methanol-containing chloroform, and finally changed to 3% methanol-containing chloroform) to obtain 309 mg of the titled compound as a waxy solid.

$[α]_D^{26}$: +24.5° (c=1.0, chloroform) $^1$H-NMR (CDCl$_3$/TMS) δ: 0.88 (9H, t, J=7Hz), 1.24 (56H, m), 1.55-1.7 (6H, m), 2.02 (1H, m), 2.1-2.5 (9H, m), 2.59 (1H, dd, J=17Hz, 7Hz), 2.67 (2H, m), 2.87 (1H, dd, J=16Hz, 6Hz), 3.63 (1H, t, J=10Hz), 3.86 (1H, d−br), 3.93 (1H, m), 4.12 (1H, d−br), 4.22 (1H, m), 4.30 (1H, dd, J=12Hz, 2Hz), 4.40 (2H, m), 4.56 (1H, m), 4.89 (1H, d, J=4Hz), 5.04 (1H, t, J=10Hz), 5.12 (6H, m), 6.36 (1H, d, J=7Hz), 6.42 (1H, br), 6.63 (1H, d, J=9Hz), 7.34 (15H, m)

REFERENCE EXAMPLE 7

Preparation of
2-Benzyloxycarbonyl-(1-benzyloxycarbonylmethyl)ethyl
2-Deoxy-6-O-[3-diphenylphosphonoxy-2R-(tetradecanoylamino)propanoyl]-3-O-(N-dodecanoylglycyl)-2-tetradecanoylamino-α-D-glucopyranoside In 8 ml of dried methylene chloride was dissolved 436 mg of 2-benzyloxycarbonyl-1-(benzyloxycarbonylmethyl)ethyl 2-deoxy-3-O-(N-dodecanoylglycyl)-2-tetradecanoyl-amino-α-D-glucopyranoside, and 203 mg of N-t-butoxycarbonyl-O-diphenylphosphono-D-serine and 6 mg of 4-dimethylaminopyridine were added to the solution. After cooling with ice, 115 mg of dicyclohexylcarbodiimide was added thereto, followed by stirring at the same temperature for 30 minutes. To the reaction mixture was added 1 ml of methanol, followed by stirring, and the solvent was removed by distillation under reduced pressure. To the residue was added acetonitrile, the insoluble matter was removed by filtration, and the solvent was removed by distillation under reduced pressure. The residue was purified by silica gel column chromatography (eluent: 1% methanol-containing chloroform) to obtain a yellow viscous oily substance.

The oily substance (496 mg) was dissolved in 5 ml of dried methylene chloride, and 3 ml of trifluoroacetic acid was added thereto while cooling with ice, followed by stirring at the same temperature for 1 hour. The solvent was removed by distillation under reduced pressure. To the residue was added toluene, followed by distillation under reduced pressure. Toluene addition and solvent removal by distillation were repeated to obtain an oily substance.

Separately, 124 mg of myristic acid and 88 mg of 1-hydroxybenzotriazole were dissolved in 3 ml of dried tetrahydrofuran, and 119 mg of dicyclohexylcarbodiimide was added to the solution under ice-cooling. After warming to room temperature, the mixture was stirred for 2 hours, and the precipitated crystal was removed by filtration. The filtrate was combined with a solution of the above-prepared oily substance in 6 ml of dried methylene chloride while cooling with ice, and 75 μl of triethylamine was added thereto, followed by stirring at room temperature for 18 hours. The solvent was removed by distillation under reduced pressure. The residue was purified by silica gel column chromatography (eluent: 5% acetone-containing chloroform, changed en route to 1.5% methanol-containing chloroform) to obtain 288 mg of the titled compound as a pale yellow oily substance.

$[α]_D^{26}$: +20.4° (c=1.0, chloroform) $^1$H-NMR (CDCl$_3$/TMS) δ: 0.88 (9H, m), 1.24 (56H, m), 1.5-1.7 (6H, m), 2.1-2.3 (6H, m), 2.52-2.72 (3H, m), 2.86 (1H, dd, J=16Hz, 6Hz), 3.54 (1H, t, J=10Hz), 3.83 (1H, dd, J=18Hz, 5Hz), 3.93 (1H, m), 4.10 (1H, dd, J=18Hz, 6Hz), 4.19 (1H, m), 4.26 (1H, dd, J=12Hz, 2Hz), 4.35-4.5 (3H, m), 4.64 (1H, m), 4.85 (2H, d, J=4Hz and m), 5.02 (1H, t, J=10Hz), 5.12 (4H, m), 6.47 (1H, br), 6.58 (1H, d, J=7Hz), 6.65 (1H, d, J=9Hz), 7.1-7.4 (20H, m).

EXAMPLE 1

Preparation of 2-Carboxy-1-(carboxymethyl)ethyl
6-O-[3-Carboxy-2R,3R-bis(tetradecanoyloxy)-propanoyl]-2-deoxy-3-O-(N-dodecanoylglycyl)-2-tetradecanoylamino-α-D-glucopyranoside (Compound No. 1)

In 30 ml of tetrahydrofuran was dissolved 252 mg of 2-benzyloxycarbonyl-1-(benzyloxycarbonylmethyl)ethyl 6-O-[3-benzyloxycarbonyl-2R, 3R-bis (tetradecanoyloxy)propanoyl]-2-deoxy-3-O-(N-dodecanoylglycyl)-2-tetradecanoylamino-α-D-glucopyranoside, and 50 mg of 10% palladium-on-carbon was suspended in the solution, followed by vigorously stirring in a hydrogen stream at room temperature for 3 hours. The catalyst was removed by filtration, and the solvent was removed by distillation under reduced pressure. The residue was purified by thin layer chromatography (TLC) (developing solvent: chloroform:methanol:water=6:4:0.15 by volume) and then treated with a strongly acidic ion exchange resin "Dowex 50W-X2" (H$^+$ type, produced by Dow Chemical Co.). The solvent was removed by distillation under reduced pressure, and the residue was dissolved in dioxane and lyophilized to obtain 108 mg of the titled compound as a white powder. The melting point was vague.

$[\alpha]_D^{25}$: +21.6° (c=0.5, chloroform:methanol=3:1 by volume) IR (KBr) $\nu_{max}$: 3400, 1750, 1645, 1545, 1470, 1205 cm$^{-1}$ $^1$H-NMR (CDCl$_3$—CD$_3$OD (i:i)/TMS) δ: 0.89 (12H, t, J=7Hz), 1.28 (76H, s), 1.5–1.7 (8H, m), 2.2–2.3 (4H, m), 2.4–2.5 (4H, m), 2.68 (3H, m), 2.80 (1H, dd, J=16Hz, 6Hz), 3.90 and 3.96 (each 1H, AB type d, J=18Hz), 3.97 (1H, m), 4.17 (1H, dd, J=11 Hz, 3Hz), 4.35–4.5 (3H, m), 4.95 (1H, d, J=3Hz), 5.06 (1H, t, J=10Hz), 5.78 (2H, br).

EXAMPLE 2

Preparation of 2-Carboxy-1-(carboxymethyl) ethyl 6-O-[4-Carboxy-2R-(tetradecanoylamino)-butanoyl]-2-deoxy-3-O-(N-dodecanoylglycyl)-2-tetradecanoylamino-α-D-glucopyranoside (Compound No. 2)

In 30 ml of tetrahydrofuran was dissolved 293 mg of 2-benzyloxycarbonyl-1- (benzyloxycarbonylmethyl-)ethyl 6-O-[4-benzyloxycarbonyl-2R- (tetradecanoyamino)butanoyl]-2-deoxy-3-O-(N-dodecanoylglycyl)-2-tetradecanoylamino-α-D-glucopyranoside, and 80 mg of 10% palladium-on-carbon was added thereto, followed by vigorously stirring in a hydrogen stream at room temperature for 2 hours. The catalyst was removed by filtration, and the solvent was removed by distillation under reduced pressure. The residue was purified by TLC ( developing solvent: chloroform:methanol :water=6:4:0.6 by volume ) and then treated with a strongly acidic ion exchange resin "Dowex 50W-X2" (H$^+$ type). The solvent was removed by distillation under reduced pressure, and the residue was dissolved in dioxane and lyophilized to obtain 177 mg of the titled compound as a white powder. The product had a vague melting point and became caramel-like at around 125° to 130° C.

$[\alpha]_D^{26}$: +30.3° (c=0.5, chloroform:methanol=3:1 by volume) IR (KBr) $\nu_{max}$: 3350, 1730, 1650,1545, 1210 cm$^{-1}$ $^1$H-NMR (CDCl$_3$—CD$_3$OD (1:1)/TMS) δ: 0.89 (9H, t, J=7Hz), 1.27 (56H, s), 1.55–1.7 (6H, m) , 2.01 (1H, m), 2.15–2.3 (7H, m), 2.44 (2H, t, J=7Hz), 2.67 (3H, m), 2.80 (1H, dd, J=16Hz, 7Hz ), 3.65 ( 1H, t, J=10Hz ), 3.90 and 3.97 (each 1H, AB type d, J=18Hz ), 4.00 (1H, m), 4.16 ( 1H, dd, J=11Hz, 3Hz) , 4.35 (1H, dd, J=12Hz, 5Hz), 4.44 (2H, m), 4.52 (1H, dd, J=8Hz, 6Hz) , 4.99 (1H, d, J=4Hz), 5.07 (1H, t, J=10Hz)

EXAMPLE 3

Preparation of 2-Carboxy-1-(carboxymethyl)ethyl 2-Deoxy-3-O-(N-dodecanoylglycyl)-6-O-[3-phosphonoxy-2R-(tetradecanoylamino)propyl]-2-tetradecanoylamino-α-D-glucopyranoside (Compound No. 3)

In 30 ml of tetrahydrofuran was dissolved 259 mg of 2-benzyloxycarbonyl-1-(benzyloxycarbonylmethyl-)ethyl 2-deoxy-6-O-[3-diphenylphosphonoxy-2R-(tetradecanoylamino)propanoyl]-3-O-(N-dodecanoylglycyl)-2-tetradecanoylamino-α-D-glucopyranoside, and 70 mg of 10% palladium-on-carbon was added thereto, followed by vigorously stirring in a hydrogen stream at room temperature for 2 hours. To the reaction mixture was further added 140 mg of platinum dioxide, followed by vigorously stirring in a hydrogen stream at room temperature for 24 hours. The catalysts were removed by filtration, and the solvent was removed by distillation under reduced pressure. The residue was purified by TLC (developing solvent: chloroform:methanol:water=6:4:0.8) and then-treated with a strongly acidic ion exchange resin "Dowex 50W-X2" (H$^+$ type). The solvent was removed by distillation under reduced pressure, and the residue was dissolved in dioxane and lyophilized to obtain 117 mg of the titled compound as a white powder. The product had a vague melting point and turned brown at about 145° C.

$[\alpha]_D^{26}$: +27.1° (C=0.5, chloroform:methanol=3:1 by volume) IR (KBr) $\nu_{max}$: 3350, 1745, 1720, 1645, 1550, 1210, 1030 cm$^{-1}$ $^1$H-NMR (CDCl$_3$—CD$_3$OD (1:1)/TMS) δ: 0.89 (9H, t, J=7Hz), 1.27 (56H, s—m), 1.5–1.7 (6H, m), 2.2–2.3 (6H, m), 2.67 (3H, m), 2.80 (1H, dd, J=16Hz, 7Hz), 3.62 (1H, t, J=10Hz), 3.90 (1H, AB type d, J=18Hz), 3.95 (1H, AB type d, J=18Hz), 4.01 (1H, m), 4.15 (1H, dd, J=11Hz, 4Hz), 4.23 (1H, m), 4.4–4.5 (4H, m), 4.80 (1H, m), 5.00 (1H, d, J=4Hz), 5.07 (1H, t, J=10Hz)

EXAMPLE 4

Step 1:

Preparation of 2-Benzyloxycarbonyl-1-(benzyloxycarbonylmethyl-)ethyl 6-O-[2R-(8-Benzoylaminooctanoylamino)-4-benzyloxycarbonylbutanoyl]-2-deoxy-3-O-(N-dodecanoylglycyl)-2-tetradecanoylamino-α-D-glucopyranoside 2-Benzyloxycarbonyl-1-(benzyloxycarbonylmethyl-)ethyl 6-O-[4-benzyloxycarbonyl-2R-(t-butoxycarbonylamino)butanoyl]-2-deoxy-3-O-(N-dodecanoylglycyl)-2-tetradecanoylamino-α-D-glucopyranoside (prepared from 2-benzyloxycarbonyl-1-(benzyloxycarbonylmethyl) ethyl 2-deoxy-3-O-(N-dodecanoylglycyl)-2-tetradecanoylamino-α-D-glucopyranoside and γ-benzyl N-t-butoxycarbonyl-D-glutamate in the same manner as in Reference Example 6) weighing 374 mg was reacted with 117 mg of 8-benzoylaminooctanoic acid in the same manner as in Reference Example 6 to obtain 312 mg of the titled compound as a white waxy solid.

$[\alpha]_D^{26}$: +25.8° (C=1:1, chloroform) $^1$H-NMR (CDCl$_3$/TMS) δ: 0.87 (6H, t, J=7Hz), 1.24 (44H, m), 1.60 (8H, m), 2.01 (1H, m), 2.16 (5H, m), 2.24 (2H, t, J=7Hz), 2.44 (2H, m), 2.59 (1H, dd, J=16Hz, 7Hz), 2.66 (2H, m), 2.84 (1H, dd, J=16Hz, 6Hz), 3.42 (2H, q, J=7Hz), 3.64 (1H, t, J=10Hz), 3.88 (1H, dd, J=18Hz, 4Hz), 3.91 (1H, m), 4.10 (1H, dd, J=18Hz, 5Hz), 4.22 (2H, m), 4.40 (1H, m), 4.47 (1H, dd, J=12Hz, 5Hz), 4.52 (1H, m), 4.89 (1H, d, J=4Hz), 5.05 (1H, t, J=10Hz), 5.1 (6H, m), 6.36 (1H, br), 6.42 (1H, br), 6.44 (1H, d, J=7Hz), 6.57 (1H, d, J=9Hz), 7.3–7.5 (18H, m), 7.77 (2H, m)

Step 2:

Preparation of 2-Carboxyl-1-(carboxymethyl)ethyl 6-O-[2R-(8-Benzoylaminooctanoylamino)-4carboxybutanoyl]-2-deoxy-3-O-(N-dodecanoylglycyl)-2-tetradecanoylamino-α-D-glucopyranoside (Compound No. 4).

The compound obtained in Step 1 above (280 mg) was reduced in a hydrogen stream in the presence of 10% palladium-on-carbon in the same manner as in Example 1 to obtain 140 mg of the titled compound as a white powder.

$[\alpha]_D^{25}$: +30.1° (c=0.6, chloroform:methanol=3:1 by volume) IR (KBr): 3320, 1740, 1640, 1550, 1205 cm$^{-1}$ $^1$H-NMR ( CDCl$_3$—CD$_3$OD (1:1)/TMS ) δ: 0.89 (6H, t, J=7Hz), 1.20 (44H, s), 1.64 (8H, m), 2.02 (1H, m), 2.2–2.3 (7H, m), 2.44 (2H, t, J=7Hz), 2.67 (3H, m), 2.80 (1H, dd, J=16Hz, 7Hz), 3.39 (2H, t, J=7Hz), 3.64 (1H, t, J=10Hz), 3.90 and 3.97 (each 1H, AB type d, J=18Hz), 3.97 (1H, m), 4.16 (1H, dd, J=11Hz, 4Hz), 4.34 (1H, dd, J=12Hz, 5Hz), 4.43 (2H, m), 4.52 (1H, dd, J=8Hz, 6Hz), 4.99 (1H, d, J=3Hz), 5.08 (1H, t, J=10Hz), 7.4-7.5 (3H, m), 7.70 (2H, m)

EXAMPLE 5

Step 1:

Preparation of 2-(Diphenylphosphonoxy)ethyl 6-O-[4-Benzyloxycarbonyl-2R-(t-butoxycarbonylamino)butanoyl]-2-deoxy-3-O-tetradecanoyl-2-tetradecanoylamino-α-D-glucopyranoside In 10 ml of dried methylene chloride were dissolved 309 mg of 2-(diphenylphosphonoxy)ethyl 2-deoxy-3O-tetradecanoyl-2-tetradecanoylamino-α-D-glucopyranoside and 137 mg of δ-benzyl N-t-butoxycarbonyl-D-glutamate, and 4 mg of dimethylaminopyridine and 87 mg of dicyclohexylcarbodiimide were added thereto under ice-cooling, followed by stirring for 45 minutes. Methanol was added to the reaction mixture, followed by stirring. The insoluble matter was removed by filtration, and the solvent was removed from the filtrate by distillation under reduced pressure. The residue was purified by column chromatography on silica gel (developing solvent: 0.5% methanol-containing chloroform) to obtain 297 mg of the titled compound as an oily substance.

$[\alpha]_D^{25}$: +27.2° (C=1.5, chloroform) $^1$H-NMR (CDCl$_3$/TMS) δ: 0.88 (6H, t, J=7Hz), 1.25 (40H, m), 1.43 (9H, s), 1.45–1.74 (m), 1.98 (1H, m), 2.04 (2H, m), 2.18 (1H, m), 2.30 (2H, m), 2.48 (2H, m), 3.64 (2H, m), 3.83 (1H, m), 3.90 (1H, m), 4.30 (3H, m), 4.40 (2H, m), 4.48 (1H, m), 4.76 (1H, d, J=3.5Hz), 5.07 (1H, t, J=10Hz), 5.12 (2H, m), 5.18 (1H, d, J=7.5Hz), 6.41 (1H, d, J=8.5Hz), 7.1-7.4 (15H, m)

Step 2:

Preparation of 2-(Diphenylphosphonoxy)ethyl 6-O-(4-Benzyloxycarbonyl-2R-tetradecanoylaminobutanoyl)-2-deoxy3-O-tetradecanoyl-2-tetradecanoylamino-α-D-glucopyranoside In 4 ml of dried methylene chloride was dissolved 280 mg of the compound obtained in Step 1 above, and 4 ml of trifluoroacetic acid was added thereto under ice-cooling, followed by stirring at that temperature for 1.5 hours. The solvent was removed by distillation under reduced pressure, and the residue was dissolved in chloroform. The solution was washed successively with water and a saturated sodium hydrogencarbonate aqueous solution, and dried over anhydrous sodium sulfate. The solvent was removed by distillation under reduced pressure to obtain an oily substance.

Separately, 83 mg of tetradecanoic acid and 49 mg of 1-hydroxybenzotriazole were dissolved in 2 ml of dried tetrahydrofuran, and 75 mg of dicyclohexylcarbodiimide was added thereto while cooling with ice. The reaction mixture was warmed to room temperature and stirred for at least 2 hours. To the reaction mixture was added the above-prepared oily substance while removing any insoluble matter precipitated therein by filtration, and the resulting mixture was stirred at room temperature for 17 hours. The solvent was removed by distillation under reduced pressure, and the residue was purified by silica gel column chromatography (developing solvent: 5% acetone-containing chloroform) to obtain 217 mg of the titled compound as a white solid.

$[\alpha]_D^{25}$: +27.1° (c=1.4, chloroform) $^1$H-NMR (CDCl$_3$/TMS) δ: 0.88 (9H, t, J=7Hz), 1.28 (60H, m), 1.94 (1H, m), 2.14–2.23 (3H, m), 2.33 (4H, m), 2.48 (2H, m), 3.67 (2H, m), 3.83 (1H, m), 3.89 (1H, m), 4.28 (2H, m), 4.39 (2H, m), 4.49 (1H, dd, J=12Hz, 4.5Hz), 4.55 (1H, m), 4.76 (1H, d, J=4Hz), 5.06 (1H, t, J=10Hz), 5.12 (2H, m), 6.34 (1H, d, J=7.5Hz), 6.38 (1H, d, J=10Hz), 7.2-7.4 (15H, m)

Step 3:

Preparation of 2-Phosphonoxyethyl 6-O-(4-Carboxy-2R-tetradecanoylaminobutanoyl)-2-deoxy-3-O-tetradecanoyl-2-tetradecanoylamino-α-D-glucopyranoside (Compound No. 5)

In a mixed solvent of 30 ml of tetrahydrofuran and 1.5 ml of distilled water was dissolved 205 mg of the compound obtained in Step 2 above, and 60 mg of 10% palladium-on-carbon was added thereto, followed by stirring in a hydrogen atmosphere at room temperature for 90 minutes. To the reaction mixture was further added 120 mg of platinum dioxide, followed by further stirring in a hydrogen atmosphere at room temperature for 3 hours. The catalysts were removed by filtration, and the solvent was removed by distillation under reduced pressure. The residue was purified by silica gel TLC (developing solvent: chloroform:methanol:water=6:4:0.7). The desired compound obtained was dissolved in a mixed solvent of tetrahydrofuran and water (9:1), and the solution was passed through a column packed with a strongly acidic ion exchange resin "Dowex 50W-X2" (H$^+$ type). The solvent was removed from the effluent by distillation under reduced pressure, and the residue was suspended in dioxane and lyophilized to obtain 112 mg of the titled compound as a white powder.

Melting point: 165°–170° C. (decomposition) $[\alpha]_D^{25}$: +31.7° (C=0.7, chloroform:methanol=3:1 by volume) IR (KBr): 3420, 1730, 1550, 1205 cm$^{-1}$ $^1$H-NMR (CDCl$_3$—CD$_3$OD (1:1)/TMS) δ: 0.89 (9H, t, J=7Hz), 1.28 (60H, bs), 1.59 (6H, m), 2.01 (1H, m), 2.17 (3H, m), 2.27 (2H, m), 2.35 (2H, m), 2.43 (2H, m), 3.67 (2H, m), 3.92 (2H, m), 4.19 (3H, m), 4.36 (1H, dd, J=12Hz, 4.5Hz), 4.43 (1H, m), 4.49 (1H, dd, J=8.5Hz, 6Hz), 4.80 (1H, d, J=3.5Hz), 5.16 ( 1H, dd, J=10.5Hz, 9.5Hz)

EXAMPLE 6

Step 1:

Preparation of 2-Benzyloxycarbonyl-2-(benzyloxycarbonylmethyl)ethyl 6-O-[4-Benzyloxycarbonyl-2R-(t-butoxycarbonylamino)butanoyl]-2-deoxy-3-O-tetradecanoyl-2-tetradecanoylamino-α-D-glucopyranoside In the same manner as in Example 5, Step 1, 2-benzyloxycarbonyl-1-(benzyloxycarbonylmethyl)ethyl-2-deoxy-3-O-tetradecanoyl-2-tetradecanoylamino-α-D-glucopyranoside and δ-benzyl N-t-butoxycarbonyl-D-glutamate were reacted to obtain the titled compound as a colorless oily substance.

[α]$_D^{25}$: +24.0° (c=0.4, chloroform) ¹H-NMR (CDCl₃/TMS) δ: 0.88 (6H, J=7.5Hz), 1.25 (br), 1.43 (9H, s), 1.5–1.7 (4H, m), 1.95 (m), 2.13 (3H, m), 2.31 (2H, m), 2.45 (2H, m), 2.65 (3H, m), 2.81 (1H, dd, J=16.5Hz, 6Hz), 3.48 (1H, m), 3.64 (1H, m), 3.86 (1H, m), 4.35 (4H, m), 4.41 (1H, m), 4.49 (1H, m), 4.88 (1H, d, J=3.5Hz), 4.98 (1H, t, J=10Hz), 5.11 (6H, m), 5.25 (1H, d, J=7.5Hz), 6.25 (1H, d, J=9.5Hz), 7.34 (15H, m)

Step 2:

Preparation of 2-Benzyloxycarbonyl-1-(benzyloxycarbonylmethyl)ethyl 6-O-[2R-(8-Benzoylaminooctanoylamino)-4-benzyloxycarbonylbutanoyl]-2-deoxy-3-O-tetradecanoyl-2-tetradecanoylamino-α-D-glucopyranoside The compound obtained in Step 1 above was reacted with 8-benzoylaminooctanoic acid in the same manner as in Example 5, Step 2 to obtain the titled compound as a white powder.

[α]$_D^{25}$: +22.4° (C=0.7, chloroform) ¹H-NMR (CDCl₃/TMS) δ: 0.88 (6H, t, J=7Hz), 1.25 (br), 1.50–1.75 (4H, m), 1.9–2.2 (6H, m), 2.31 (1H, m), 2.46 (1H, m), 2.62 (3H, m), 2.70 (1H, dd, J=16Hz, 6Hz), 3.44 (2H, m), 3.67 (1H, m), 3.87 (1H, m), 4.24 (2H, m), 4.41 (1H, m), 4.50 (2H, m), 4.87 (1H, d, J=3.5Hz), 5.00 (1H, t, J=10Hz), 5.10 and 5.13 (total 6H, each s), 6.24 (1H, d, J=10Hz), 6.32 (1H, m), 6.46 (1H, d, J=7.5Hz), 7.3–7.5 (18it, m), 7.76 (2H, m)

Step 3:

Preparation of 2-Carboxy-1-(carboxymethyl)ethyl 6-O-[2R-(8-Benzoylaminooctanoylamino)-4-carboxybutanoyl]-2-deoxy-3-O-tetradecanoyl-2-tetradecanoylamino-α-D-glucopyranoside (Compound No. 6)

The compound obtained in Step 2 above was reduced in the same manner as in Example 1 to obtain the titled compound as a white powder.

[α]$_D^{25}$: +40.0° (c=0.1, methanol) IR (KBr): 3350, 1730, 1640, 1545 cm⁻¹ ¹H-NMR (CDCl₃—CD₃OD (1:1)/TMS) δ: 0.88 (6H, t, J=7.5Hz), 1.25 (br), 1.5–1.7 (m), 2.02 (1H, m), 2.19 (3H, m), 2.26 (2H, m), 2.32 (2H, m), 2.45 (2H, t, J=7.5Hz), 2.68 (3H, m), 2.79 (1H, dd, J=16.5Hz, 6Hz), 3.35 (2H, m), 3.63 (1H, t, J=9.5Hz), 3.97 (3H, m), 4.15 (1H, dd, J=10.5Hz, 3.5Hz), 4.37 (2H, m), 4.44 (1H, m), 4.49 (1H, m), 4.97 (1H, d, J=3.5Hz), 5.07 (1H, t, J=10.5Hz), 7.44 (2H, m), 7.50 (1H, m), 7.80 (2H, m)

EXAMPLE 7

Step 1:

Preparation of 2-Benzyloxycarbonyl-1-(benzyloxycarbonylmethyl)ethyl 6-O-[2R-(6-Benzoylaminohexanoylamino)-4-benzyloxycarbonylbutanoyl]-2-deoxy-3-O-tetradecanoyl-2-tetradecanoylamino-α-D-glucopyranoside The compound obtained in Example 6, Step 1 was reacted with 6-benzoylaminohexanoic acid in the same manner as in Example 5, Step 2 to obtain the titled compound as a white powder.

Melting point: 97°–101° C. [α]$_D^{25}$: +26.b 4° (C=0.9, chloroform) ¹H-NMR (CDCl₃/TMS) δ: 0.88 (6H, m), 1.25 (br), 1.5–1.8 (m), 1.9–2.5 (m), 2.62 (3H, m), 2.80 (1H, dd, J=16Hz, 6Hz), 3.45 (2H, q, J=6.5Hz), 3.66 (1H, t, J=9.5Hz), 3.87 (1H, m), 4.18 (1H, m), 4.23 (1H, m), 4.40 (1H, m), 4.48 (2H, m), 4.87 (1H, d, J=3.5Hz), 5.01 (1H, t, J=10Hz), 5.12 (6H, m), 6.26 (1H, d, J=9.5z), 6.53 (1H, d, J=7.5Hz), 6.62 (1H, m), 7.3–7.5 (18H, m), 7.78 (2H, m)

Step 2:

Preparation of 2-Carboxy-1-(carboxymethyl)ethyl 6-O-[2R-(6-Benzoylaminohexanoylamino)-4-carboxybutanoyl]-2-deoxy-3-O-tetradecanoyl-2-tetradecanoylamino-α-D-glucopyranoside (Compound No. 7)

The compound obtained in Step 1 above was reacted in the same manner as in Example 1. The product was purified by high performance liquid chromatography using an ODS reverse phase column (developing solvent: methanol: water:acetic acid:triethylamine=40:1:0.1:0.15) and further worked up in the same manner as in Example 1 to obtain the titled compound as a white powder.

[α]$_D^{25}$: +35.0° (C=0.3, methanol) IR (KBr): 3385, 1730, 1645, 1540 cm⁻¹ ¹H-NMR (CDCl₃—CD₃OD (1:1)/TMS) δ: 0.88 (6H, m), 1.25 (br), 1.45 (2H, m), 1.57 (2H, m), 1.67 (2H, m), 2.02 (1H, m), 2.18 (3H, m), 2.30 (4H, m), 2.45 (2H, t, J=7.5Hz), 2.68 (3H, m), 2.79 (1H, dd, J=16.5Hz, 6Hz), 3.41 (2H, m), 3.64 (1H, t, J=9.5Hz), 3.97 (1H, m), 4.15 (1H, dd, J=10.5Hz, 3.5Hz), 4.36 (2H, m), 4.44 (1H, m), 4.49 (1H, m), 4.97 (1H, d, J=3.5Hz), 5.06 (1H, t, J=10.5Hz), 7.44 (2H, m), 7.51 (1H, m), 7.81 (2H, m)

EXAMPLE 8

Step 1:

Preparation of 2-Methoxycarbonyl-1-(methoxycarbonylmethyl)ethyl 3,4,6-Tri-O-acetyl-2-(8-benzoylaminooctanoylamino)-2-deoxy-α-D-glucopyranoside In 10 ml of acetic acid was dissolved 1.096 g of 2-methoxycarbonyl-1-(methoxycarbonylmethyl)ethyl-3,4,6-tri-O-acetyl-2-deoxy-2-(2,2,2-trichloroethoxycarbonylamino)-α-D-glucopyranoside, and zinc powder was added thereto in small portions while vigorously stirring at room temperature until the starting compound disappeared. Any insoluble matter was removed by filtration, the filtrate was washed with chloroform, and the solvent was removed by distillation under reduced pressure. Toluene was added to the residue, followed by distillation under reduced pressure. Toluene addition and the following distillation were repeated. The residue was dissolved in chloroform, washed successively with a 5% sodium hydrogencarbonate aqueous solution and a saturated sodium chloride aqueous solution, and dried over anhydrous sodium sulfate. The solvent was removed by distillation under reduced pressure to obtain an oily substance.

The resulting oily substance was dissolved in 15 ml of dried methylene chloride, and 0.50 g of 8-benzoylaminooctanoic acid was added thereto. After once cooling with ice, 0.39 g of dicyclohexylcarbodiimide and 20 mg of dimethylaminopyridine were added thereto, followed by stirring at room temperature for 14 hours. The precipitated insoluble matter was removed by filtration, and the filtrate was washed successively with 1N hydrochloric acid, a 5% sodium hydrogencarbonate aqueous solution, and a saturated sodium chloride aqueous solution, and dried over anhydrous sodium sulfate. The solvent was removed by distillation under reduced pressure, and the residue was purified by column chromatography on silica gel (developing solvent: 5% acetone-containing chloroform, changed en route to 2% methanol-containing chloroform) to obtain 1.162 g of the titled compound as a colorless, viscous and oily substance.

$[\alpha]_D^{25}$: +41.0° (c=1.5, chloroform) $^1$H-NMR (CDCl$_3$/TMS) δ: 1.36 (6H, m), 1.60 (2H, m), 1.70 (2H, m), 1.98 (3H, s), 2.02 (3H, s), 2.09 (3H, s), 2.20 (2H, m), 2.59 (1H, dd, J=16Hz, 6.5Hz), 2.66 (2H, ABq), 2.81 (1H, dd, J=16Hz, 5.5Hz), 3.44 (2H, q, J=7Hz), 3.69 (3H, s), 3.72 (3H, s), 4.04 (1H, m), 4.10 (1H, dd, J=12Hz, 2Hz), 4.20 (1H, dd, J=12Hz, 4.5Hz), 4.35 (1H, td, J=10Hz, 3.5Hz), 4.41 (1H, m), 4.96 (1H, d, J=4Hz), 5.09 (1H, t, J=10Hz), 5.14 (1H, t, J=10Hz), 6.24 (1H, br), 6.34 (1H, d, J=9Hz), 7.4-7.5 (3H, m), 7.76 (2H, m)

Step 2:

Preparation of
2-Methoxycarbonyl-1-(methoxycarbonylmethyl)ethyl
2-(8-Benzoylaminooctanoylamino)-2-deoxy-α-D-glucopyranoside In 15 ml of dried methanol was dissolved 1.152 g of the compound obtained in Step 1 above, and a methanol solution of sodium methoxide prepared from 18 mg of metallic sodium was added thereto while cooling with ice, followed by stirring at the same temperature for 30 minutes. The reaction mixture was neutralized by addition of a non-aqueous strongly acidic ion exchange resin "Amberlist 15-E". The resin was removed by filtration, and the solvent was removed by distillation under reduced pressure. The residue was solidified by treating with chloroform and hexane, and dried to obtain 827 mg of the titled compound as a white solid. An aliquot of the product was recrystallized from a mixed solvent of hexane and chloroform.

Melting point: 118°-120° C. $[\alpha]_D^{25}$: +71.8° (C=0.7, methanol) IR (KBr): 3350, 1740, 1710, 1645, 1540, 1030 cm$^{-1}$ $^1$H-NMR (CDCl$_3$/TMS) δ: 1.36 (6H, m), 1.62 (4H, m), 2.31 (2H, t, J=7Hz), 2.55 (1H, dd, J=16Hz, 6Hz), 2.66 (2H, m), 2.78 (1H, dd, J=16Hz, 6.5Hz), 3.43 (2H, q, J=7Hz), 3.70 (3H, s), 3.73 (3H, s), 3.99 (1H, m), 4.43 (1H, m), 4.95 (1H, d, J=4Hz), 6.34 (1H, br), 7.12 (1H, br), 7.4–7.5 (3H, m), 7.75 (2H, m)

Step 3:

Preparation of
2-Benzyloxycarbonyl-1-(benzyloxycarbonylmethyl-)ethyl
2-(8-Benzoylaminooctanoylamino)-2-deoxy-α-D-glucopyranoside In a mixed solvent of 10 ml of tetrahydrofuran and 2 ml of water was dissolved 616 mg of the compound obtained in Step 2 above, and 3.17 ml of a 1N sodium hydroxide aqueous solution was added thereto under ice-cooling, followed by stirring at that temperature for 1 hour. The reaction mixture was neutralized by addition of a weakly acidic ion exchange resin "MWC-1". The resin was removed by filtration, the filtrate was washed with ethanol, and the solvent was removed by distillation under reduced pressure. Ethanol addition and removal were repeated, and the residue was dried in vacuo in the presence of phosphorus pentoxide to obtain a yellow semisolid. The product was dissolved in 8 ml of dried dimethylformamide, and 0.88 ml of triethanolamine and 0.75 ml of benzyl bromide were added thereto. The mixture was heated to 50° to 60° C. and stirred at that temperature for 1.5 hours. The solvent was removed by distillation under reduced pressure, and the residue was dissolved in ethyl acetate, washed successively with 1N hydrochloric acid, water, and a saturated sodium chloride aqueous solution, and dried over anhydrous sodium sulfate. The solvent was removed by distillation under reduced pressure, and the residue was purified by silica gel column chromatography (developing solvent: 2% methanol-containing chloroform, changed en route to 5% methanol-containing chloroform ) to obtain 465 mg of the titled compound as a colorless caramel-like semisolid.

$[\alpha]_D^{25}$: +16.1° (C=1.0, chloroform) IR (KBr): 3310, 1735, 1640, 1540, 1025 cm$^{-1}$ $^1$H-NMR (CDCl$_3$/TMS) δ: 1.36 (6H, m), 1.61 (4H, m), 2.26 (2H, m), 2.58 (1H, dd, J=16Hz, 6Hz), 2.66 (1H, dd, J=16.5Hz, 3.5Hz), 2.73 (1H, dd, J=16.5Hz, 8.5Hz), 2.81 (1H, dd, J=16.5Hz, 6.5Hz), 3.42 (2H, m), 3.49 (1H, t, J=9Hz), 3.59 (1H, t, J=9.5Hz), 3.69 (2H, m), 3.81 (1H, m), 3.95 (1H, m), 4.45 (1H, m), 4.92 (1H, d, J=3.5Hz), 5.13 (2H, s), 5.16 (2H, s), 6.19 (1H, br), 7.09 (1H, d, J=7.5Hz), 7.3–7.5 (13H, m), 7.74 (2H, m)

Step 4:

Preparation of
2-Benzyloxycarbonyl-1-(benzyloxycarbonylmethyl-)ethyl
2-(8-Benzoylaminooctanoylamino)-2-deoxy-3-O-tetradecanoyl-α-D-glucopyranoside In 8 ml of dried methylene chloride was dissolved 571 mg of the compound obtained in Step 3 above, and 0.96 ml of 2,2-dimethoxypropane and 9 mg of camphorsulfonic acid were added to the solution at room temperature, followed by stirring at room temperature for 4 hours. To the reaction mixture was added about 0.1 ml of triethylamine, followed by stirring for neutralization. The reaction mixture was washed successively with water and a saturated sodium chloride aqueous solution, and dried over anhydrous sodium sulfate. The solvent was removed by distillation under reduced pressure. The resulting oily substance was dissolved in 10 ml of dried methylene chloride, and 75 μl of pyridine, 5 mg of dimethylaminopyridine, and 230 mg of tetradecanoyl chloride were successively added thereto under ice-cooling, followed by stirring at that temperature for 3 hours. Further, 0.31 mg of pyridine and 300 mg of the same acid chloride were added, and the mixture was stirred at room temperature for 18 hours. The reaction mixture was washed successively with 1N hydrochloric acid, water, and a saturated sodium chloride aqueous solution, and dried over anhydrous sodium sulfate. The solvent was removed by distillation under reduced pressure. The oily residue was dissolved in 30 ml of a 90% acetic acid aqueous solution and stirred at 90° C. for 30 minutes. After cooling, the solvent was removed by distillation under reduced pressure. Toluene was added to the residue and then removed by distillation under reduced pressure. Toluene addition and removal were repeated, and the residue was purified by silica gel column chromatography (developing solvent: 5% acetone-containing chloroform, changed en route to 2% methanol-containing chloroform). Hexane was added to the product to solidify, followed by filtration to recover 633 mg of the titled compound as a white powder.

[α]$_D^{25}$: +34.1° (c=1.3, chloroform) IR (KBr): 3340, 1735, 1650, 1635, 1540, 1150, 1030 cm$^{-1}$ $^1$H-NMR (CDCl$_3$/TMS) δ: 0.87 (3H, t, J=7Hz), 1.24 (26H, s), 1.62 (6H, m), 2.14 (2H, m), 2.32 (2H, m), 2.64 (3H, m), 2.77 (1H, dd, J=17Hz, 7Hz), 3.42 (2H, q, J=6.5Hz), 3.71 (4H, m), 4.23 (1H, td, J=10Hz, 3.5Hz), 4.46 (1H, m), 4.90 (1H, d, J=3.5Hz), 4.96 (1H, dd, J=10.5Hz, 9Hz), 5.10 (1H, AB type d, J=12Hz), 5.14 (2H, s), 5.15 (1H, AB type d, J=12Hz), 6.18 (1H, br), 6.33 (1H, d, J=9Hz), 7.3–7.5 (13H, m), 7.75 (2H, m)

Step 5:

Preparation of 2-Benzyloxycarbonyl-1-(benzyloxycarbonylmethyl)ethyl 2-(8-Benzoylaminooctanoylamino)-6-O-[4-benzyloxycarbonyl-2R-(t-butoxycarbonylamino)butanoyl]-2-deoxy-3-O-tetradecanoyl-α-D-glucopyranoside The compound obtained in step 4 above was reacted in the same manner as in Example 5, Step 1 to obtain the titled compound as a colorless, viscous and oily substance.

[α]$_D^{25}$: +19.9° (c=0.9, chloroform) $^1$H-NMR (CDCl$_3$/TMS) δ: 0.87 (3H, t, J=7Hz), 1.24 (26H, s), 1.42 (9H, s), 1.60 (6H, m), 1.98 (1H, m), 2.13 (3H, m), 2.30 (2H, m), 2.46 (2H, m), 2.64 (3H, m), 2.81 (1H, dd, J=16.5Hz, 6Hz), 3.42 (2H, q, J=6.5Hz), 3.65 (1H, br), 3.86 (1H, m), 4.41 (1H, m), 4.88 (1H, d, J=3.5Hz), 4.98 (1H, t, J=10Hz), 5.11 (6H, m). 5.24 (1H, d–br), 6.16 (1H, br), 6.30 (1H, d, J=9.5Hz), 7.3–7.5 (18H, m), 7.74 (2H, m)

Step 6:

Preparation of 2-Benzyloxycarbonyl-1-(benzyloxycarbonylmethyl)ethyl 2-(8-Benzoylaminooctanoylamino)-6-O-(4-benzyloxycarbonyl-2R-tetradecanoylaminobutanoyl)-2-deoxy-3-O-tetradecanoyl-α-D-glucopyranoside The compound obtained in Step 5 above was reacted with tetradecanoic acid in the same manner as in Example 5, Step 2 to obtain the titled compound as a white waxy solid.

[α]$_D^{25}$: +23.2° (c=0.9, chloroform) $^1$H-NMR (CDCl$_3$/TMS)δ: 0.87 (6H, m), 1.24 (46H, m), 1.59 (8H, m), 2.04 (1H, m), 2.15 (5H, m), 2.31 (2H, m), 2.47 (2H, m), 2.64 (3H, m), 2.80 (1H, dd, J=16Hz, 6Hz), 3.42 (2H, q, J=7Hz), 3.67 (1H, m), 3.87 (1H, m), 4.21 (2H, m), 4.41 (1H, m), 4.51 (2H, m), 4.89 (1H, d, J=4Hz), 4.99 (1H, t, J=10Hz), 5.11 (6H, m), 6.16 (1H, br), 6.29 (1H, d, J=9.5Hz), 6.36 (1H, d, J=7.5Hz), 7.3–7.5 (18H, m), 7.74 (2H, m)

Step 7:

Preparation of 2-Carboxy-1-(carboxymethyl)ethyl 2-(8-Benzoylaminooctanoylamino)-6-O-(4-carboxy-2R-tetradecanoylaminobutanoyl)-2-deoxy-3-O-tetradecanoyl-α-D-glucopyranoside (Compound No. 8)

The compound obtained in Step 6 above was reacted and worked up in the same manner as in Example 1 to obtain the titled compound as a white powder.

[α]$_D^{25}$: +39.5° (c=0.5, methanol) IR (KBr): 3340, 1730, 1635, 1545 cm$^{-1}$ $^1$H-NMR (CDCl$_3$—CD$_3$OD (1:1)/TMS) δ: 0.89 (6H, m), 1.27 (46H, m), 1.60 (8H, m), 2.02 (1H, m), 2.15–2.4 (7H, m), 2.45 (2H, t, J=7.5Hz), 2.66 (3H, m), 2.79 (1H, dd, J=16Hz, 6.5Hz), 3.39 (2H, t, J=7Hz), 3.66 (1H, t, J=9.5Hz), 3.97 (1H, m), 4.15 (1H, dd, J=11Hz, 3.5Hz), 4.38 (2H, m), 4.44 (1H, m), 4.49 (1H, dd, J=8.5Hz, 6Hz), 4.97 (1H, d, J=3.5Hz), 5.06 (1H, t, J=10Hz), 7.46 (3H, m), 7.79 (2H, m)

EXAMPLE 9

Step 1:

Preparation of 2-Benzyloxycarbonyl-1-(benzyloxycarbonylmethyl)ethyl 6-O-[4-Benzyloxycarbonyl-2S-(t-butoxycarbonylamino)butanoyl]-2-deoxy-3-O-tetradecanoyl-2-tetradecanoylamino-α-D-glucopyranoside 2-Benzyloxycarbonyl-1-(benzyloxycarbonylmethyl)ethyl 2-deoxy-3-O-tetradecanoyl-2-tetradecanoylamino-α-D-glucopyranoside and δ-benzyl N-t-butoxycarbonyl-L-glutamate were reacted in the same manner as in Example 5, Step 1 to obtain the titled compound as a colorless oily substance.

[α]$_D^{25}$S: +22.7° (c=1.0, chloroform) $^1$H-NMR (CDCl$_3$/TMS) δ: 0.88 (6H, J=7Hz), 1.25 (40H, br), 1.44 (9H, s), 1.61 (4H, m), 1.93 (1H, m), 2.10 (3H, m), 2.31 (2H, m), 2.42 (2H, m), 2.66 (3H, m), 2.80 (1H, dd, J=16.5Hz, 6Hz), 3.63 (1H, m), 3.88 (1H, m), 4.26 (2H, m), 4.4 (3H, m), 4.89 (1H, d, J=3.5Hz), 5.00 (1H, t, J=10Hz), 5.11 (6H, m), 5.20 (1H, d, J=7.5Hz), 6.25 (1H, d, J=9.5Hz), 7.3–7.4 (15H, m)

Step 2:

Preparation of 2-Benzyloxycarbonyl-1(benzyloxycarbonylmethyl)ethyl 6-O-(4-Benzyloxycarbonyl-2S-tetradecanoylaminobutanoyl)-2-deoxy-3-O-tetradecanoyl-2-tetradecanoylamino-α-D-glucopyranoside The compound obtained in Step 1 above was reacted with tetradecanoic acid in the same manner as in Example 5, Step 2 to obtain the titled compound as a white waxy solid.

[α]$_D^{25}$: +27.3° (C=1.9, chloroform) $^1$H-NMR (CDCl$_3$/TMS) δ: 0.88 (9H, t, J=6.5Hz), 1.25 (60H, s), 1.59 (6H, m), 1.92 (1H, m), 2.13 (3H, m), 2.31 (4H, m), 2.42 (2H, m), 2.66 (3H,m), 2.79 (1H, dd, J=16.5Hz, 6Hz), 3.61 (1H, m), 3.88 (1H, m), 4.26 (2H, m), 4.36 (2H, m), 4.61 (1H, m), 4.89 (1H, d, J=3.5Hz), 5.01 (1H, m), 5.1 (6H, m), 6.27 (1H, d, J=9.5Hz), 6.34 (1H, d, J=7Hz), 7.3–7.4 (15H, m)

Step 3:

Preparation of 2-Carboxy-1-(carboxymethyl)ethyl 6-O-(4-Carboxy-2S-tetradecanoylaminobutanoyl)-2-deoxy-3-O-tetradecanoyl-2-tetradecanoylamino-α-D-glucopyranoside (Compound No. 9)

The compound obtained in Step 2 above was reacted in the same manner as in Example 1. The product was purified by silica gel TLC (developing solvent: chloroform: methanol: 50% ammonium acetate aqueous solution=6:4:0.5) and then further worked up in the same manner as in Example 1 to obtain the titled compound as a white powder.

[α]$_D^{25}$: +24.1° (c=0.6, methanol) IR (KBr): 3300, 1660, 1470, 1170, 1055 cm$^{-1}$ $^1$H-NMR (CDCl$_3$—CD$_3$OD (1:1)/TMS) δ: 0.89 (9H, t, J=7Hz), 1.28 (60H, m), 1.60 (6H, m), 2.02 (1H, m), 2.20 (3H, m), 2.23–2.39 (4H, m), 2.43 (2H, m), 2.65–2.71 (3H, m), 2.77 (1H, dd, J=16Hz, 7Hz), 3.54 (1H, t, J=10Hz), 3.99 (1H, m), 4.13 (1H, dd, J=11Hz, 4Hz), 4.30 (1H, dd, J=12Hz, 5Hz), 4.42–4.47 (2H, m), 4.52 (1H, dd, J=9Hz, 5Hz), 4.97 (1H, d, J=4Hz), 5.07 (1H, t, J=10Hz)

EXAMPLE 10

Step 1:

Preparation of
2-Benzyloxycarbonyl-1-(benzyloxycarbonylmethyl-
)ethyl
3-O-Benzyloxycarbonyl-2-deoxy-2-tet-
radecanoylamino-α-D-glucopyranoside In 15 ml of dried methylene chloride was dissolved 2.32 g of 2-benzyloxycarbonyl-1-(benzyloxycarbonylmethyl)ethyl 2-deoxy-2-tetradecanoylamino-α-D-glucopyranoside, and 2.04 ml of 2,2-dimethoxypropane and 38 mg of camphorsulfonic acid were added thereto at room temperature, followed by stirring at room temperature for 15 hours. Further, 20 mg of camphorsulfonic acid and 2.04 ml of 2,2-dimethoxypropane were added thereto, and the stirring was continued for an additional period of 8 hours. The reaction mixture was neutralized with anhydrous potassium carbonate while stirring, washed successively with water and a saturated sodium chloride aqueous solution, and dried over anhydrous sodium sulfate. The solvent was removed by distillation under reduced pressure. The resulting yellow oily substance was dissolved in 20 ml of dried methylene chloride, and 0.40 ml of pyridine, 0.61 g of N,N-dimethylaminopyridine, and 0.71 ml of benzyloxycarbonyl chloride were successively added thereto at room temperature, followed by stirring at room temperature for 12 hours. The reaction mixture was washed successively with 1N hydrochloric acid, water, and a saturated sodium chloride aqueous solution, and dried over anhydrous sodium sulfate. The solvent was removed by distillation under reduced pressure. The resulting yellow oily substance was dissolved in 50 ml of a 90% acetic acid aqueous solution, and the solution was stirred at 90° C. for 30 minutes. After cooling, the solvent was removed by distillation under reduced pressure. Toluene was added to the residue and then removed by distillation under reduced pressure. Toluene addition and removal were repeated, and the resulting residue was purified by silica gel column chromatography (developing solvent: 5% acetone-containing chloroform, changed en route to 2% methanol-containing chloroform) to obtain a pale yellow oily substance. Recrystallization from hexane followed by filtration gave 2.42 g of the titled compound as a white solid. This solid could be recrystallized from hexane.

Melting point: 80°–82° C. $[\alpha]_D^{25}$: +46.5° (c=0.8, chloroform) IR (KBr): 3350, 1750, 1730, 1650, 1275, 1260 cm$^{-1}$ $^1$H-NMR (CDCl$_3$/TMS) δ: 0.88 (3H, t, J=7Hz), 1.22 (20H, s), 1.52 (2H, m), 2.0–2.1 (2H, m), 2.64 (3H, m), 2.77 (1H, dd, J=16Hz, 6Hz), 3.75 (4H, m), 4.26 (1H, td, J=10Hz, 3Hz ), 4.46 ( 1H, m ), 4.82 (1H, dd, J=11Hz, 8Hz), 4.92 (1H, d, J=4Hz ), 5.10 ( 1H, AB type d, J=12Hz), 5.13 (4H, s), 5.14 (1H, AB type d, J=12Hz ), 6.31 ( 1H, d, J=9Hz), 7.3–7.4 (15H, m)

Step 2:

Preparation of
2-Benzyloxycarbonyl-1-(benzyloxycarbonylmethyl-
)ethyl
3-O-Benzyloxycarbonyl-6-O-[3-benzyloxycarbonyl-
2R,3R-bis(tetradecanoyloxy)-propanoyl]-2-deoxy-2-tet-
radecanoylamino-α-D-glucopyranoside The compound obtained in Step 1 above was reacted with monobenzyl 2,3-bis-O-tetradecanoyl-L-tartrate in the same manner as in Reference Example 1 to obtain the titled compound as a colorless, viscous and oily substance.

$[\alpha]_D^{25}$: +27.8° ( c=1.0, chloroform) $^1$H-NMR (CDCl$_3$/TMS) δ: 0.88 (9H, t, J=7Hz), 1.25 (60H, m), 1.54 (6H, m), 2.04 (2H, m), 2.11 (1H, m), 2.26 (1H, m), 2.39 (2H, m), 2.65 (3H, m), 2.77 (1H, dd, J=16Hz, 6Hz), 3.60 (1H, td, J=9.5Hz, 5Hz), 3.85 (1H, m), 4.20 (1H, dd, J=12Hz, 2Hz ) , 4.28 (1H, m), 4.42 ( 1H, m), 4.49 (1H, dd, J=12Hz, 4Hz ), 4.79 (1H, dd, J=10.5Hz, 9.5Hz), 4.90 (1H, d, J=3.5Hz), 5.14 (8H, m), 5.70 (1H, d, J=3Hz), 5.76 (1H, d, J=3Hz), 6.23 (1H, t, J=10Hz), 7.3–7.4 (20H, m)

Step 3:

Preparation of 2-Carboxy-1-(carboxymethyl)ethyl
6-O-[3-Carboxy-2R,3R-bis(tetradecanoyloxy)-
propanoyl]-2-deoxy-2-tetradecanoylamino-α-D-
glucopyranoside (Compound No. 10)

The compound obtained in Step 2 above was reduced in the same manner as in Example 1 to obtain the titled compound as a white powder.

$[\alpha]_D^{25}$: +40.7° (C=0.5, methanol) IR (KBr): 3450, 1740, 1220, 1150 cm$^{-1}$ $^1$H-NMR (CDCl$_3$—CD$_3$OD (1:1)/TMS) δ: 0.89 (12H, t, J=6.5Hz), 1.27 (60H, s), 1.64 (6H, m), 2.28 (2H, m), 2.44 (4H, m), 2.66 (3H, m), 2.78 (1H, dd, J=16Hz, 6.5Hz), 3.41 (1H, t, J=9.5Hz), 3.56 (1H, t, J=10Hz), 3.86 (1H, m), 3.96 (1H, dd, J=10.5Hz, 3.5Hz), 4.39 (2H, m), 4.46 (1H, d, J=11Hz), 4.94 (1H, d, J=3.5Hz), 5.78 (2H, s)

EXAMPLE 11

Step 1:

Preparation of
2-Benzyloxycarbonyl-1(benzyloxycarbonylmethyl-
)ethyl
3-O-(8-Benzoylaminooctanoyl)-2-deoxy-2-tet-
radecanoylamino-α-D-glucopyranoside In the same manner as in Example 8, Step 4, 2-benzyloxycarbonyl-1-(benzyloxycarbonylmethyl)ethyl 2-deoxy-2-tetradecanoylamino-α-D-glucopyranoside was once protected with an isopropylidene group and then reacted with 8-benzoylaminooctanoic acid, followed by removal of the isopropylidene group to obtain the titled compound as a colorless oily substance.

$[\alpha]_D^{25}$: +33.6° (c=0.5, chloroform) $^1$H-NMR (CDCl$_3$/TMS) δ: 0.87 (3H, t, J=7.5Hz), 1.23 (br), 1.36 (br), 1.62 (br), 2.12 (2H, m), 2.32 (2H, m), 2.58–2.82 (4H, m), 3.43 (2H, q, J=7.5Hz), 3.7–3.8 (4H, m), 4.23 (1H, td, J=9.5Hz, 4Hz), 4.45 (1H, m), 4.90 (1H, d, J=4Hz), 5.01 (1H, m), 5.13 (4H, m), 6.31 (2H, m), 7.3–7.8 (15H, m)

Step 2:

Preparation of
2-Benzyloxycarbonyl-1-(benzyloxycarbonylmethyl)ethyl
3-O-(8-Benzoylaminooctanoyl)-6-O-[4-benzyloxycarbonyl-2R-(t-butoxycarbonylamino)butanoyl]-2-deoxy-2-tetradecanoylamino-α-D-glucopyranoside The compound obtained in Step 1 above was reacted with δ-benzyl N-t-butoxycarbonyl-D-glutamate in the same manner as in Example 5, Step 1 to obtain the titled compound as a colorless oily substance.

$[\alpha]_D^{25}$: +22.2° (c=0.5, chloroform) $^1$H-NMR (CDCl$_3$/TMS) δ: 0.88 (3H, J=7.5Hz), 1.25 (br), 1.43 (9H, s), 1.5–1.7 (4H, m), 1.95 (1H, m), 2.13 (2H, m), 2.32 (2H, m), 2.44 (2H, m), 2.65 (3H, m), 2.81 (1H, dd, J=16.5Hz, 6Hz), 3.44 (2H, m), 3.65 (1H, m), 3.87 (1H, m), 4.24 (3H, m), 4.42 (2H, m), 4.86 (1H, d, J=3.5Hz), 5.00 (1H, t, J=10Hz), 5.13 (6H, m), 5.27 (1H, d—br), 6.28 (2H, m), 7.3–7.5 (18H, m), 7.75 (2H, m)

Step 3:

Preparation of
2-Benzyloxycarbonyl-1-(benzyloxycarbonylmethyl)ethyl
3-O-(8-Benzoylaminooctanoyl)-6-O-(4-benzyloxycarbonyl-2R-tetradecanoylaminobutanoyl)-2-deoxy-2-tetradecanoylamino-α-D-glucopyranoside The compound obtained in Step 2 above was reacted with tetradecanoic acid in the same manner as in Example 5, Step 2 to obtain the titled compound as a white powder.

Melting Point: 84°–86 °C. $[\alpha]_D^{25}$: +25.3° (c=0.9, chloroform) $^1$H-NMR (CDCl$_3$/TMS) δ: 0.88 (6H, m), 1.25 (br), 1.50–1.65 (4H, m), 2.0–2.5 (m), 2.62 (3H, m), 2.82 (1H, dd, J=16Hz, 6Hz), 3.43 (2H, q, J=7Hz), 3.68 (1H, m), 3.88 (1H, m), 4.23 (2H, m), 4.40 (1H, m), 4.46 (1H, m), 4.53 (1H, m), 4.87 (1H, d, J=3.5Hz), 5.02 (1H, t, J=10Hz), 5.12 (6H, m), 6.27 (1H, d, J=9.5Hz), 6.37 (1H, m), 6.42 (1H, d, J=7.5Hz), 7.3–7.5 (18H, m), 7.76 (2H, m)

Step 4:

Preparation of 2-Carboxy-1-(carboxymethyl)ethyl
3-O-(8-Benzoylaminooctanoyl)-6-O-(4-carboxy-2R-tetradecanoylaminobutanoyl)-2-deoxy-2-tetradecanoylamino-α-D-glucopyranoside (Compound No. 11).

The compound obtained in Step 3 above was reacted, and the product was purified and worked up in the same manner as in Example 7, Step 2 to obtain the titled compound as a white powder.

$[\alpha]_D^{25}$: +45.2° (c=0.3, methanol) IR (KBr): 3355, 1730, 1635, 1580 cm$^{-1}$ $^1$H-NMR (CDCl$_3$—CD$_3$OD (1:1)/TMS) δ: 0.88 (6H, m), 1.25 (br), 1.5–1.7 (m), 2.02 (1H, m), 2.15–2.40 (m), 2.45 (2H, t, J=7.5Hz), 2.68 (3H, m), 2.79 (1H, dd, J=16.5Hz, 6Hz), 3.39 (2H, m), 3.64 (1H, t, J=9.5Hz), 3.97 (1H, m), 4.15 (1H, dd, J=10.5Hz, 3.5Hz), 4.37 (2H, m), 4.44 (1H, m), 4.50 (1H, m), 4.97 (1H, d, J=2.5Hz), 5.06 (1H, t, J=10.5Hz), 7.44 (2H, m), 7.50 (1H, m), 7.80 (2H, m)

EXAMPLE 12

Step 1:

Preparation of
2-Methoxycarbonyl-1(methoxycarbonylmethyl)ethyl
3,4,6-Tri-O-acetyl-2-deoxy-2-tetradecanoylamino-β-D-glucopyranoside 2-Methoxycarbonyl-1-(methoxycarbonylmethyl)ethyl 3,4,6-tri-O-acetyl-2-deoxy-2-(2,2,2-trichloroethoxycarbonylamino)-β-D-glucopyranoside was reacted with tetradecanoic acid in the same manner as in Example 8, Step 1 to obtain the titled compound as a white waxy solid.

$[\alpha]_D^{25}$: −3.1° (c=1.9, chloroform) IR (KBr): 3560, 3330, 1745, 1660 cm$^{-1}$ $^1$H-NMR (CDCl$_3$/TMS) δ: 0.88 (3H, t, J=7Hz), 1.25 (br), 1.54 (2H, m), 2.00 (3H, s), 2.02 (3H, s), 2.07 (2H, m), 2.08 (3H, s), 2.5–2.65 (3H, m), 2.92 (1H, dd, J=16.5Hz, 5Hz), 3.67 (3H, s), 3.68 (3H, s), 4.00 (1H, q, J=9Hz), 4.10 (1H, dd, J=11Hz, 2.5Hz), 4.24 (1H, dd, J=11Hz, 5Hz), 4.40 (1H, m), 4.47 (1H, m), 4.77 (1H, d, J=9Hz), 5.05 (1H, t, J=9.5Hz), 5.12 (1H, t, J=9.5Hz), 5.62 (1H, d, J=9Hz)

Step 2:

Preparation of
2-Methoxycarbonyl-1-(methoxycarbonylmethyl)ethyl
2-Deoxy-2-tetradecanoylamino-β-D-glucopyranoside The compound obtained in Step 1 above was reacted in the same manner as in Example 8, Step 2 to obtain the titled compound as a white powder. $^1$H-NMR (CDCl$_3$/TMS) δ: 0.88 (3H, t, J=7Hz), 1.25 (br), 1.63 (2H, m), 2.2–2.35 (2H, m), 2.49-2.77 (5H, m), 2.81 (1H, dd, J=15.5Hz, 7Hz), 3.38–3.57 (4H, m), 3.73 (3H, s), 3.74 (3H, s), 3.92 (1H, dd, J=12Hz, 2.5Hz), 4.45 (1H, m), 4.58 (1H, d, J=8.5Hz), 6.90 (1H, br )

Step 3:

Preparation of
2-Benzyloxycarbonyl-1-(benzyloxycarbonylmethyl)ethyl
2-Deoxy-2-tetradecanoylamino-β-D-glucopyranoside The compound obtained in Step 2 above was reacted in the same manner as in Example 8, Step 3 to obtain the titled compound as a white waxy solid.

$[\alpha]_D^{25}$: −23.9° (c=1.0, chloroform) IR (KBr): 3430, 3320, 1740, 1655, 1550 cm$^{-1}$ $^1$H-NMR (CDCl$_3$/TMS) δ: 0.88 (3H, t, J=7Hz), 1.25 (br), 1.61 (2H, m), 2.21 (2H, m), 2.56 (1H, dd, J=16Hz, 5.5Hz), 2.65 (1H, dd, J=16Hz, 3.5Hz), 2.74 (1H, m), 2.82 (1H, dd, J=16.5Hz, 6.5Hz), 3.25–3.45 (4H, m), 3.59 (1H, m), 3.83 (1H, dd, J=12Hz, 3.5Hz), 4.00 (1H, q, J=9Hz ), 4.20 (2H, m), 5.08–5.24 (4H, m), 6.84 (1H, m), 7.35 (1OH, m)

Step 4:

Preparation of
2-Benzyloxycarbonyl-1-(benzyloxycarbonylmethyl)ethyl
2-Deoxy-3-O-tetra-decanoyl-2-tetradecanoylamino-β-D-glucopyranoside The compound obtained in Step 3 above was reacted in the same manner as in Example 8, Step 4 to obtain the titled compound as a white powder.

$[\alpha]_D^{25}$: −18.9° (C=1.3, Chloroform) IR (KBr): 3340, 1750, 1730, 1670 cm$^{-1}$ $^1$H-NMR (CDCl$_3$/TMS) δ:

0.88 (3H, t, J=7Hz), 1.25 (br), 1.50 (2H, m), 1.57 (2H, m), 1.99 (2H, m), 2.32 (3H, m), 2.51 (1H, dd, J=15.5Hz, 6Hz), 2.56 (1H, dd, J=16.5Hz, 3.5Hz), 2.65 (1H, dd, J=16.5Hz, 9.5Hz), 2.79 (1H, dd, J=15.5Hz, 7Hz), 3.34 (1H, m), 3.49 (1H, t, J=9.5Hz), 3.59 (1H, m), 3.87 (2H, m), 4.51 (1H, m), 4.53 (1H, d, J=8.5Hz), 4.80 (1H, dd, J=10.5Hz, 8.5Hz), 5.02 (1H, AB type d, J=12Hz), 5.13 (1H, AB type d, J=12.5Hz), 5.14 (1H, AB type d, J=12.5Hz), 5.22 (1H, AB type d, J=12.5Hz), 5.38 (1H, d, J=9Hz), 7.3–7.4 (10H, m)

Step 5:

Preparation of 2-Benzyloxycarbonyl-1-(benzyloxycarbonylmethyl)ethyl 6-O-[4-Benzyloxycarbonyl-2R-(t-butoxycarbonylamino)butanoyl]-2-deoxy-3-O-tetradecanoyl-2-tetradecanoylamino-β-D-glucopyranoside The compound obtained in Step 4 above was reacted in the same manner as in Example 5, Step 1 to obtain the titled compound as a colorless waxy substance.

$[\alpha]_D^{25}$: −10.3° (c=0.6, chloroform) IR (KBr): 3360, 1730, 1670, 1535 cm$^{-1}$ $^1$H-NMR (CDCl$_3$/TMS) δ: 0.88 (6H, t, J=7Hz), 1.25 (br), 1.42 (9H, s), 1.45–1.6 (4H, m), 1.98 (3H, m), 2.14 (1H, m), 2.31 (2H, m), 2.4–2.6 (3H, m), 2.87 (1H, dd, J=16.5Hz, 5Hz), 3.48 (1H, m), 3.63 (1H, m), 3.88 (1H, m), 4.26 (2H, m), 4.41 (1H, m), 4.49 (1H, m), 4.53 (1H, d, J=8.5Hz), 4.83 (1H, t, J=10Hz), 5.01 (1H, AB type d, J=12Hz), 5.10 (4H, m), 5.20 (1H, AB type d, J=12Hz), 5.30 (1H, d, J=9Hz), 7.34 (15H, m)

Step 6:

Preparation of 2-Benzyloxycarbonyl-1(benzyloxycarbonylmethyl)ethyl 6-O-(4-Benzyloxycarbonyl-2R-tetradecanoylaminobutanoyl)-2-deoxy-3-O-tetradecanoyl-2-tetradecanoylamino-β-D-glucopyranoside The compound obtained in Step 5 above was reacted with tetradecanoic acid in the same manner as in Example 5, Step 2 to obtain the titled compound as a white powder.

Melting Point: 107°–109° C. $[\alpha]_D^{25}$: −8.8° (C=0.6, chloroform) IR (KBr): 3340, 1740, 1670, 1625, 1550 cm$^{-1}$ $^1$H-NMR (CDCl$_3$/TMS) δ: 0.88 (9H, t, J=7Hz), 1.25 (br), 1.5–1.75 (6H, m), 1.9–2.6 (m), 2.87 (1H, dd, J=16Hz, 5Hz), 3.40 (1H, m), 3.64 (1H, t, J=9.5Hz), 3.89 (1H, m), 4.29 (1H, m), 4.4–4.5 (3H, m), 4.52 (1H, d, J=8.5Hz), 4.83 (1H, t, J=10Hz), 5.01 (1H, AB type d, J=12Hz), 5.11 (4H, m), 5.20 (1H, AB type d, J=12Hz), 5.32 (1H, d, J=9Hz), 6.47 (1H, d, J=7Hz), 7.34 (15H, m)

Step 7:

Preparation of 2-Carboxy-1-(carboxymethyl)ethyl 6-O-(4-Carboxy-2R-tetradecanoylaminobutanoyl)-2-deoxy-3-O-tetradecanoyl-2-tetradecanoylamino-β-D-glucopyranoside (Compound No. 12)

The compound obtained in Step 6 above was reacted in the same manner as in Example 9, Step 3 to obtain the titled compound as a white powder.

Melting Point: 204°–205° C. (decomposition) $[\alpha]_D^{25}$: −7.0° (c=0.2, methanol) IR (KBr): 3380, 1730, 1660, 1620, 1550 cm$^{-1}$ $^1$H-NMR (DMSO-d$_6$/TMS) δ: 0.86 (9H, t, J=7Hz), 1.24 (br), 1.35–1.5 (m), 1.62–2.02 (m), 2.08 2.31 (m), 2.42–2.5 (m), 2.59 (1H, dd, J=16.5Hz, 6,5Hz), 3.55 (1H, m), 3.78 (1H, m), 3.83 (1H, m), 4.13 (1H, m), 4.26 (1H, m), 4.31 (2H, m), 4.60 (1H, d, J=8Hz), 4.87 (1H, t, J=10.5Hz), 5.33 (1H, 12.09 (3H, s)

EXAMPLE 13

Step 1:

Preparation of 2-Benzyloxycarbonyl-1-(benzyloxycarbonylmethyl)ethyl 6-O-[4-Benzyloxycarbonyl-2R-(4-octanoylaminobenzoylamino)butanoyl]-2-deoxy-3-O-tetradecanoyl-2-tetradecanoylamino-α-D-glucopyranoside The compound obtained in Example 6, Step 1 was reacted with p-octanoylaminobenzoic acid in the same manner as in Example 5, Step 2 to obtain the titled compound as a white powder.

$[\alpha]_D^{25}$: +24.5° (c=0.9, chloroform) IR (KBr): 3320, 1740, 1660, 1620 cm$^{-1}$ $^1$H-NMR (CDCl$_3$/TMS) δ: 0.88 (9H, m), 1.25 (br), 1.9–2.65 (m), 2.78 (1H, dd, J=16.5Hz, 6.5Hz), 3.68 (1H, m), 3.88 (1H, m), 4.21 (2H, m), 4.40 (1H, m), 4.53 (1H, m), 4.67 (1H, m), 4.87 (1H, d, J=3.5Hz), 4.98 (1H, t, J=10Hz), 5.10 (6H, m), 6.27 (1H, d, J=9.5Hz), 7.3–7.4 (19H, m), 7.61 (1H, d, J=8.5Hz, 7.77 (1H, d, J=8.5Hz)

Step 2:

Preparation of 2-Carboxy-1-(carboxymethyl)ethyl 6-O-[4-Carboxy-2R-(4-octanoylaminobenzoylamino)-butanoyl]-2-deoxy-3-O-tetradecanoyl-2-tetradecanoylamino-β-D-glucopyranoside (Compound No. 13)

The compound obtained in Step 1 above was reacted in the same manner as in Example 7, Step 2 to obtain the titled compound as a white powder. The product had a vague melting point and turned brown at about 195° C. $[\alpha]_D^{25}$: +30.1° (C=0.3, methanol) IR (KBr): 3320, 1730, 1660, 1525 cm$^{-1}$ $^1$H-NMR (CDCl$_3$—CD$_3$OD (1:1)/TMS) δ: 0.90 (9H, m), 1.28 (br), 1.60 (4H, m), 1.72 (2H, m), 2.2–2.4 (m), 2.5 2.65 (m), 2.75 (1H, dd, J=17.5Hz, 6Hz), 3.64 (1H, t, J=9.5Hz), 3.98 (1H, m), 4.14 (1H, dd, J=11Hz, 3.5Hz), 4.40 (3H, m), 4.96 (1H, d, J=3.5Hz), 5.06 (1H, t, J=10.5Hz), 7.69 (2H, d, J=9Hz), 7.84 (2H, d, J=9Hz)

EXAMPLE 14

Step 1:

Preparation of 2-Benzyloxycarbonyl-1-(benzyloxycarbonylmethyl)ethyl 6-O-[4-Benzyloxycarbonyl-2R-(4-octanoylaminophenylacetamido)butanoyl]-2-deoxy-3-O-O-tetradecanoyl-2-tetradecanoylamino-α-D-glucopyranoside The compound obtained in Example 6, Step 1 was reacted with p-octanoylaminophenylacetic acid in the same manner as in Example 5, Step 2 to obtain the titled compound as a white waxy solid.

$[\alpha]_D^{25}$: +20.5° (c=0.8, chloroform) IR (KBr): 3310, 1740, 1650, 1630, 1610 cm$^{-1}$ $^1$H-NMR (CDCl$_3$/TMS) δ: 0.88 (9H, t, J=7Hz), 1.25 (br), 1.55–1.75 (m), 1.95–2.45 (m), 2.67 (1H, m), 2.76 (1H, dd, J=16Hz, 6.5Hz), 3.45 (2H, q, J=6.5Hz), 3.50

(3H, m), 3.84 (1H, m), 4.02 (1H, m), 4.19 (1H, m), 4.43 (1H, m), 4.47 (1H, m), 4.54 (1H, m), 4.92 (1H, d, J=4Hz), 5.01 (1H, t, J=10Hz), 5.03-5.16 (6H, m), 6.12 (1H, d, J=9Hz), 6.39 (1H, d, J=9Hz), 6.62 (1H, m), 7.20 (2H, d, J=9Hz), 7.34 (15H, m), 7.67 (2H, d, J=9Hz), 8.51 (1H, s)

Step 2:

Preparation of 2-Carboxy-1-(carboxymethyl)ethyl 6-O-[4-Carboxy-2R-(4-octanoylamino-phenylacetamido)butanoyl]-2-deoxy-3-O-tetradecanoyl-2-tetradecanoylamino-α-D-glucopyranoside (Compound No. 14)

The compound obtained in Step 1 above was reacted in the same manner as in Example 7, Step 2 to obtain the titled compound as a white powder.

Melting Point: 165°-173° C. (decomposition) [α]$_D^{25}$: +39.6° (c=0.3, methanol ) IR (KBr): 3300, 1730, 1660, 1535 cm$^{-1}$ $^1$H-NMR (CDCl$_3$—CD$_3$OD (1:1)/TMS) δ: 0.88 (9H, m), 1.27 (br), 1.57 (4H, m), 1.71 (2H, m), 2.02 (1H, m), 2.20 ( 3H, m), 2.35 (6H, m), 2.61 (1H, dd, J=16Hz, 6Hz), 2.65 (2H, d, J=6Hz), 2.76 (1H, dd, J=16Hz, 6Hz), 3.55 (2H, s), 3.60 (1H, t, J=9.5Hz), 3.95 (1H, m), 4.14 (1H, dd, J=11Hz, 3.5Hz), 4.36 (2H, m), 4.41 (1H, m), 4.50 (1H, m), 4.95 (1H, d, J=3.5Hz), 5.06 (1H, t, J=10.5Hz), 7.25 (2H, d, J=8.5Hz), 7.54 (2H, d, J=8.5Hz)

EXAMPLE 15

Step 1:

Preparation of 2-Benzyloxycarbonyl-1-(benzyloxycarbonylmethyl)ethyl 6-O-(4-Benzyloxycarbonyl-2R-tetradecanoylaminobutanoyl)-2-deoxy-3-O-tetradecanoyl-2-tetradecanoylamino-α-D-glucopyranoside The compound obtained in Example 6, Step 1 was reacted with tetradecanoic acid in the same manner as in Example 5, Step 2 to obtain the titled compound as a white waxy solid.

[α]$_D^{25}$: +18.1° (c=0.9, chloroform) $^1$H-NMR (CDCl$_3$/TMS) δ: 0.88 (9H, t, J=7Hz), 1.25 ( 60H, m) , 1.59 (4H, m), 1.67 (2H, m), 1.93 (1H, m), 1.98-2.21 (5H, m), 2.30 (2H, m), 2.44 (2H, m), 2.62 (3H, m), 2.81 (1H, dd, J=16Hz, 6Hz ) , 3.67 (1H, t, J=10Hz), 3.88 (1H, m), 4.24 (2H, m), 4.41 (1H, m). 4.51 (2H, m), 4.89 (1H, d, J=3.5Hz ) , 4.99 (1H, t, J=10Hz), 5 . 12 (4H, m) , 6.24 (1H, d, J=9Hz), 6.35 (1H, d, J=7Hz), 7.2-7.4 (15H, m)

Step 2:

Preparation of 2-Carboxy-1-(carboxymethyl)ethyl 6-O-(4-Carboxy-2R-tetradecanoylaminobutanoyl)-2-deoxy-3-O-tetradecanoyl-2-tetradecanoylamino-α-D-glucopyranoside (Compound No. 15)

The compound obtained in Step 1 above was reacted in the same manner as in Example 9, Step 3 to obtain the titled compound as a white powder.

[α]$_D^{25}$: +41.3° (c=0.6, methanol) IR (KBr): 3290, 1730, 1060 cm$^{-1}$ $^1$H-NMR (CDCl$_3$—CD$_3$OD (1:1)/TMS ) δ: 0.90 (9H, t, J=7Hz), 1.29 (60H, s), 1.55-1.62 (6H, m), 1.98 (1H, m), 2.20 (3H, m), 2.25 (2H, m), 2.31 (2H, m), 2.43 (2H, m), 2.70 (3H, m), 2.76 (1H, dd, J=15Hz, 7Hz), 3.62 (1H, t, J=10Hz), 3.97 (1H, m), 4.12 (1H, dd, J=11Hz, 4Hz), 4.32 (1H, dd, J=12Hz, 4Hz), 4.42 (1H, m), 4.43 (1H, m), 4.48 (1H, dd, J=9Hz, 6Hz), 4.99 (1H, d, J=3.5Hz), 5.06 (1H, dd, J=11Hz, 9Hz)

EXAMPLE 16

Step 1:

Preparation of 2-Benzyloxycarbonyl-1-(benzyloxycarbonylmethyl)ethyl 2-(8-Benzoylaminooctanoylamino)-6-O-[4-benzyloxycarbonyl-2R-(N-dodecanoyl-N-dodecylglycylamino)-butanoyl]-2-deoxy-3-O-tetradecanoyl-α-D-glucopyranoside The compound obtained in Example 8, Step 5 was reacted with N-dodecyl-N-dodecanoylglycine in the same manner as in Example 5, Step 2 to obtain the titled compound as a colorless oily substance.

[α]$_D^{25}$: +21.6° (c=1.3, chloroform) $^1$H-NMR (CDCl$_3$/TMS) δ: 0.87 (9H, t, J=7Hz), 1.25 (60H, m), 1.60 (10H, m), 2.03 (1H, m). 2.15 (3H, m), 2.30 (2H, m), 2.36 (2H, m), 2.43 (2H, m), 2.62 (3H, m), 2.81 (1H, dd, J=16Hz, 6Hz ) , 3.31 (2H, m), 3.42 (2H, q, J=6.5Hz ) , 3.69 (1H, m), 3.88 (1H, m), 3.91 and 3.97 (each 1H, AB type d, J=12Hz), 4.25 (2H, m), 4.41 (2H, m), 4.48 (1H, m), 4.88 (1H, d, J=3.5Hz), 5.00 (1H, t, J=10Hz), 5.10 (6H, m), 6.18 (1H, br), 6.28 (1H, d, J=9.5Hz), 7.14 (1H, d, J=7.5Hz), 7.3-7.5 (18H, m), 7.75 (2H, m)

Step 2:

Preparation of 2-Carboxy-1-(carboxymethyl)ethyl 2-(8-Benzoylaminooctanoylamino)-6-O-[4-carboxy-2R-(N-dodecanoyl-N-dodecylglycylamino)butanoyl]-2-deoxy-3-O-tetradecanoyl-α-D-glucopyranoside (Compound No. 16)

The compound obtained in Step 1 above was reacted in the same manner as in Example 9, Step 3 to obtain the titled compound as a white powder. p0 [α]$_D^{25}$: +36.0° (c=0.4, methanol) IR (KBr): 3320, 1740, 1700, 1665, 1645, 1545 cm$^{-1}$ $^1$H-NMR (CDCl$_3$—CD$_3$OD (1:1)/TMS) δ: 0.88 (9H, m), 1.27 (60H, m), 1.59 (10H, m), 2.03 (1H, m), 2.19 (3H, m), 2.31 (2H, m), 2.43 (4H, m), 2.66 (3H, m), 2.79 (1H, dd, J=16Hz, 6.5Hz), 3.39 (4H, m), 3.63 (1H, t, J=9.5Hz ), 3.98 ( 1H, m ), 3.99 and 4.06 (each 1H, AB type d, J=16Hz), 4.15 (1H, dd, J=10.5Hz, 4Hz), 4.35 (1H, dd, J=11.5Hz, 4.5Hz), 4.43 (2H, m), 4.53 (1H, dd, J=8.5Hz, 5.5Hz), 4.97 (1H, d, J=4Hz), 5.07 (1H, t, J=10Hz), 7.46 (3H, m), 7.79 (2H, m)

EXAMPLE 17

Step 1:

Preparation of 2-Benzyloxycarbonyl-1-(benzyloxycarbonylmethyl)ethyl 6-O-[4-Benzyloxycarbonyl-2R-(8-phenyloctanoylamino)butanoyl]-2-deoxy-3-O-tetradecanoyl-2-tetradecanoylamino-α-D-glucopyranoside The compound obtained in Example 6, Step 1 was reacted with 8-phenyloctanoic acid in the same manner as in Example 5, Step 2 to obtain the titled compound as a white powder.

Melting Point: 68°-70° C. [α]$_D^{25}$: +25.3° (C=2.2, chloroform) IR (KBr): 3530, 3320, 1735, 1650 cm$^{-1}$ $^1$H-NMR (CDCl$_3$/TMS) δ: 0.88 ( 6H, t, J=7Hz ) , 1.25 ( br ) , 1.55-1.70 (m), 1.9-2.7 (m), 2.81 ( 1H, dd, 16.5Hz, 6.5Hz) , 3.68 (1H, m), 3.89 (1H, m), 4.25 (2H, m), 4.42

(1H, m), 4.46 (1H, m), 4.60 ( 1H, m) , 4 . 63 (1H, m), 4.90 (1J, d, J=3.5Hz ) , 5.00 ( 1H, t, J=10Hz ), 5.12 (6H, m), 6.26 (1H, d, J=9 . 5Hz ) , 6.37 (1H, d, J=7Hz), 7.15–7.4 (20H, m)

Step 2:

Preparation of 2-Carboxy-1-(carboxymethyl)ethyl 6-O-[4-Carboxy-2R-(8-phenyloctanoylamino)-butanoyl]-2-deoxy-3-O-tetradecanoyl-2-tetradecanoylamino-α-D-glucopyranoside (Compound No. 17)

The compound obtained in Step 1 above was reacted in the same manner as in Example 7, Step 2 to obtain the titled compound as a white powder. The product had a vague melting point and turned brown at about 135° C. $[\alpha]_D^{25}$: +41.0° (C=0.4, methanol) IR (KBr): 3300, 1740, 1650, 1545 cm$^{-1}$ $^1$H-NMR (CDCl$_3$—CD$_3$OD (1:1)/TMS) δ: 0.89 (6H, t, J=7Hz), 1.28 (br), 1.6(m), 2.03 (1H, m), 2.15–2.40 (m), 2.43 (2H, t, J=7.5Hz), 2.60 (2H, t, J=7.5Hz), 2.66 (3H, m), 2.78 (1H, dd, J=17.5Hz, 6Hz), 3.61 (1H, t, J=9.5Hz), 3.99 (1H, m), 4.15 (1H, dd, J=11Hz, 3.5Hz), 4.32–4.50 (4H, m), 4.97 (1H, d, J=3.5Hz), 5.07 (1H, t, J=10.5Hz), 7.15–7.28 (5H, m)

EXAMPLE 18

Step 1:

Preparation of 2-Benzyloxycarbonyl-1-(benzyloxycarbonylmethyl-)ethyl 6-O-[4-Benzyloxycarbonyl-2R-(4-octylbenzoylamino)-butanoyl]-2-deoxy-3-O-tetradecanoyl-2-tetradecanoylamino-α-D-glucopyranoside The compound obtained in Example 6, Step 1 was reacted with p-octylbenzoic acid in the same manner as in Example 5, Step 2 to obtain the titled compound as a colorless oily substance.

$[\alpha]_D^{25}$: +12.9° (c=0.5, chloroform) $^1$H-NMR (CDCl$_3$/TMS) δ: 0.88 (9n, t, J=7Hz ), 1.25 ( br ), 1.55–1.7 (m), 1.95–2.35 (m), 2.5–2.65 (m), 2.67 (1H, m), 2.79 (1H, dd, J=16Hz, 6.5Hz), 3.72 (1H, m), 3.89 (1H, m), 4.27 (2H, m), 4.43 (1H, m), 4.55 (1H, dd, J=12Hz, 4Hz), 4.68 (1H, m), 4.90 (1H, d, J=4Hz ), 5.00 ( 1H, t, J=10Hz ), 5.11 (6H, m), 6.24 (1H, d, J=9.5Hz), 7.22 (2H, d, J=9Hz), 7.34 (15H, m), 7.70 (2H, d, J=9Hz)

Step 2:

Preparation of 2-Carboxy-1-(carboxymethyl)ethyl 6-O-[4-Carboxy-2R-(4-octylbenzoylamino)butanoyl]-2-deoxy-3-O-tetradecanoyl-2-tetradecanoylamino-β-D-glucopyranoside (Compound No. 18)

The compound obtained in Step 1 above was reacted in the same manner as in Example 7, Step 2 to obtain the titled compound as a white powder. The product had a vague melting point and turned brown at about 173° C. $[\alpha]_D^{25}$: +37.9° (c=0.4, methanol) IR (KBr): 1730, 1640, 1540 cm$^{-1}$ $^1$H-NMR (CDCl$_3$—CD$_3$OD (1:1)/TMS) δ: 0.88 (9H, t), 1.27 (br), 1.60 (m), 2.15–2.35 (m), 2.53 (2H, t, J=7.5Hz), 2.57–2.70 (m), 2.75 (1H, dd, J=16Hz, 6Hz), 3.65 (1H, t, J=9.5Hz), 3.97 (1H, m), 4.14 (1H, dd, J=11Hz, 3.5HZ), 4.41 (3H, m), 4.96 (1H, d, J=3.5Hz), 5.06 (1H, t, J=10.5Hz), 7.28 (2H, d, J=8.5Hz), 7.78 (2H, d, J=8.5Hz)

EXAMPLE 19

Step 1:

Preparation of 2-Benzyloxycarbonyl-1-(benzyloxycarbonylmethyl-)ethyl 6-O-(3-Benzyloxycarbonyl-3S-tetradecanoylamino-propanoyl)-2-deoxy-3-O-tetradecanoyl-2-tetradecanoylamino-α-D-glucopyranoside 2-Benzyloxycarbonyl-1-(benzyloxycarbonylmethyl-)ethyl 2-deoxy-3-O-tetradecanoyl-2-tetradecanoylamino-α-D-glucopyranoside and α-benzyl N-tetradecanoyl-L-aspartate were reacted in the same manner as in Example 5, Step 1 to obtain the titled compound as a colorless oily substance.

$[\alpha]_D^{25}$: +31.1° (c=0.8, chloroform) $^1$H-NMR (CDCl$_3$/TMS) δ: 0.88 (9H, t, J=7.5Hz), 1.25 (60H, s), 1.58 (6H, m), 2.12 (2H, m), 2.20 (2H, m), 2.31 (2H, m), 2.63 (3H, m), 2.74 (1H, dd, J=16Hz, 8Hz), 2.79 (1H, dd, J=16Hz, 6Hz), 2.90 (1H, dd, J=15Hz, 4Hz), 3.74 (1H, m), 3.84 (1H, m), 4.18 (1H, dd, J=12Hz, 2Hz), 4.27 (2H, m), 4.40 (1H, m), 4.91 (1H, d, J=3Hz), 5.01 (2H, m), 5.12 (4H, m), 5.17 and 5.23 (each 1H, AB type d, J=12Hz), 6.24 (1H, d, J=9Hz), 6.38 (1H, d, J=9Hz), 7.36 (15H, m)

Step 2:

Preparation of 2-Carboxy-1-(carboxymethyl)ethyl 6-O-(3-Carboxy-3S-tetradecanoylaminopropanoyl)-2-deoxy-3-O-tetradecanoyl-2-tetradecanoylamino-β-D-glucopyranoside (Compound No. 19)

The compound obtained in Step 1 above was reacted in the same manner as in Example 9, Step 3 to obtain the titled compound as a white powder.

$[\alpha]_D^{25}$: +35.6° (C=0.6, methanol) IR (KBr): 3430, 1730, 1180 cm$^{-1}$ $^1$H-NMR (CDCl$_3$—CD$_3$OD (1:1)/TMS) δ: 0.89 (9H, t, J=6Hz), 1.28 (60H, s), 1.50–1.68 (6H, m), 2.23 (4H, m), 2.32 (2H, m), 2.66 (3H, m), 2.77 (1H, dd, J=14Hz, 6Hz), 2.95 (2H, m), 3.62 (1H, t, J=10Hz), 3.96 (1H, m), 4.15 (1H, m), 4.32 (1H, dd, J=12Hz, 4Hz), 4.42 (2H, m), 4.83 (1H, m), 4.99 (1H, d, J=3Hz), 5.07 (1H, t, J=10Hz)

EXAMPLE 20

Step 1:

Preparation of 2-Benzyloxycarbonyl-1-(benzyloxycarbonylmethyl-)ethyl 6-O-(3-Benzyloxycarbonyl-3S-tetradecanoyloxy-propanoyl)-2-deoxy-3-O-tetradecanoyl-2-tetradecanoylamino-α-D-glucopyranoside 2-Benzyloxycarbonyl-1-(benzyloxycarbonylmethyl-)ethyl 2-deoxy-3-O-tetradecanoyl-2-tetradecanoylamino-α-D-glucopyranoside and α-benzyl O-tetradecanoyl-L-malate were reacted in the same manner as in Example 5, Step 1 to obtain the titled compound as a colorless oily substance.

$[\alpha]_D^{25}$: +15.9° (C=1.2, chloroform) $^1$H-NMR (CDCl$_3$/TMS) δ: 0.88 (9H, t, J=7Hz), 1.25 (60H, s), 2.12 (2H, m), 2.30 (2H, m), 2.36 (2H, m), 2.66 (3H, m), 2.79 (1H, dd, J=16Hz, 6Hz), 2.81 (2H, m), 3.58 (1H, m), 3.83 (1H, m), 4.24 (2H, m), 4.36 (1H, dd, J=12Hz, 4Hz ), 4.42 ( 1H, m), 4.89 ( 1H, d, J=4Hz), 4,98 (1H, t, J=10Hz), 5.00 (4H, m), 5.15 and 5.21 (each 1H, AB type d, J=12Hz), 5.54 (1H, dd, J=8Hz, 5Hz ), 6.24 ( 1H, d, J=9Hz ), 7.34 (15H, m)

Step 2:

Preparation of 2-Carboxy-1-(carboxymethyl)-ethyl 6-O-(3-Carboxy-3S-tetradecanoyloxypropanoyl)-2-deoxy-3-O-tetradecanoyl-2-tetradecanoylamino-α-D-glucopyranoside (Compound No. 20)

The compound obtained in Step 1 above was reacted in the same manner as in Example 9, Step 3 to obtain the titled compound as a white powder.

$[\alpha]_D^{26}$: +27.8° (C=0.6, methanol) IR (KBr): 3390, 1740, 1170 cm$^{-1}$ $^1$H-NMR (CDCl$_3$—CD$_3$OD (1:1)/TMS) δ: 0.90 ( 9H, t, J=6Hz ), 1.29 (60H, s), 1.50–1.68 (6H, m), 2.20 (2H, t, J=7Hz ), 2.31 ( 2H, m), 2.40 (2H, t, J=7Hz), 2.67 (3H, m), 2.77 (2H, dd, J=16Hz, 6Hz), 2.93 (1H, dd, J=17Hz, 8Hz), 3.00 (1H, dd, J=17Hz, 4Hz), 3.55 (1H, t, J=10HZ), 3.96 (1H, m), 4.11 (1H, dd, J=10Hz, 3Hz) , 4.33 (1H, m), 4.41 (2H, m), 4.99 ( 1H, d, J=3Hz ), 5.06 (1H, t, J=10Hz), 5.42 (1H, m)

EXAMPLE 21

Step 1:

Preparation of 2-Benzyloxycarbonyl-1-(benzyloxycarbonylmethyl)ethyl 6-O-[3-Benzyloxycarbonyl-2S-(t-butoxycarbonylamino)propanoyl]-2-deoxy-3-O-tetradecanoyl-2-tetradecanoylamino-α-D-glucopyranoside 2-Benzyloxycarbonyl-1-(benzyloxycarbonylmethyl)ethyl 2-deoxy-3-O-tetradecanoyl-2-tetradecanoylamino-α-D-glucopyranoside and β-benzyl N-t-butoxycarbonyl-L-aspartate were reacted in the same manner as in Example 5, Step 1 to obtain the titled compound as a colorless oily substance.

$[\alpha]_D^{25}$: +27.5° (c:0.8, chloroform) $^1$H-NMR (CDCl$_3$/TMS) δ: 0.86 (6H, t, J=6Hz), 1.24 (40H, br), 1.44 (9H, s), 1.56 (4H, m), 2.12 (2H, m), 2.29 (2H, m), 2.63 (3H, m), 2.79 (1H, m), 2.88 (1H, m), 3.05 (1H, dd, J=17Hz, 4Hz), 3.55 (1H, m), 3.85 (1H, m), 4.22 (2H, m), 4.40 (1H, m), 4.47 (1H, dd, J=12Hz, 4Hz) , 4.58 ( 1H, m) , 4.83 (1H, d, J=4Hz), 4.98 (1H, t, J=10Hz ), 5.13 ( 6H, m), 5.51 (1H, d, J=7.5Hz ), 6.22 ( 1H, d, J=9.5Hz), 7.3–7.4 (15H, m)

Step 2:

Preparation of 2-Benzyloxycarbonyl-1-(benzyloxycarbonylmethyl)ethyl 6-O-(3-Benzyloxycarbonyl-2S-tetradecanoylaminopropanoyl)-2-deoxy-3-O-tetradecanoyl-2-tetradecanoylamino-α-D-glucopyranoside The compound obtained in Step 1 above was reacted with tetradecanoic acid in the same manner as in Example 5, Step 2 to obtain the titled compound as a white waxy solid.

$[\alpha]_D$: +28.8° (c=0.7, chloroform) $^1$H-NMR (CDCl$_3$/TMS) δ: 0.88 (9H, t, J=7Hz), 1.25 (60H, br), 1.56 (6H, m), 2.04–2.22 (4H, m), 2.27 (2H, m), 2.62 (3H, m), 2.77 (1H, dd, J=16Hz, 6Hz), 2.90 (1H, dd, J=17Hz, 4Hz), 3.06 (1H, dd, J=17Hz, 4Hz), 3.55 (1H, t, J=10Hz), 3.85 (1H, m), 4.21 (1H, td, J=10Hz, 4Hz), 4.27 (1H, dd, J=12Hz, 2Hz), 4.40 (1H, m), 4.44 (1H, dd, J=12Hz, 4Hz), 4.82 (1H, d, J=4Hz), 4.86 (1H, m), 5.00 (1H, t, J=10Hz), 5.14 (6H, m), 6.28 (1H, d, J=9Hz ), 6.52 ( 1H, d, J=8Hz ), 7.3–7.4 (15H, m)

Step 3:

Preparation of 2-Carboxy-1-(carboxymethyl)ethyl 6-O-(3-Carboxy-2S-tetradecanoylaminopropanoyl)-2-deoxy-3-O-tetradecanoyl-2-tetradecanoylamino-α-D-glucopyranoside (Compound No. 21)

The compound obtained in Step 2 above was reacted in the same manner as in Example 9, Step 3 to obtain the titled compound as a white powder.

$[\alpha]_D^{25}$: +29.4° (C=0.5, methanol) IR (KBr): 1730, 1220 cm$^{-1}$ $^1$H-NMR (CDCl$_3$—CD$_3$OD (1:1)/TMS) δ: 0.90 (9H, m), 1.29 (60H, br), 1.60 (6H, m), 2.18–2.38 (6H, m), 2.61–2.77 (4H, m), 2.83 (1H, dd, J=17Hz, 7Hz) , 2.88 (1H, dd, J=17Hz, 5Hz), 3.56 (1H, t, J=10Hz), 3.95 (1H, m), 4.10 (1H, dd, J=10Hz, 3Hz ), 4.32 ( 1H, dd, J=12Hz, 4Hz), 4.42 (2H, m), 4.83 (1H, m), 4.98 (1H, d, J=3HZ), 5.06 (1H, t, J=10Hz)

EXAMPLE 22

Step 1:

Preparation of 2-Benzyloxycarbonyl-1-(benzyloxycarbonylmethyl)ethyl 6-O-[3-Benzyloxycarbonyl-2R-(t-butoxycarbonylamino)propanoyl]-2-deoxy-3-O-tetradecanoyl-2-tetradecanoylamino-α-D-glucopyranoside 2-Benzyloxycarbonyl-1-(benzyloxycarbonylmethyl)ethyl 2-deoxy-3-O-tetradecanoyl-2-tetradecanoylamino-α-D-glucopyranoside and β-benzyl N-t-butoxycarbonyl-D-aspartate were reacted in the same manner as in Example 5, Step 1 to obtain the titled compound as a colorless oily substance.

$[\alpha]_D^{25}$: +22.3° (C=1.2, chloroform) $^1$H-NMR (CDCl$_3$/TMS) δ: 0.88 (6H, t, J=6.5Hz), 1.24 (40H, br), 1.44 (9H, s), 2.30 (2H, m), 2.63 (3H, m), 2.79 (1H, m), 2.85 (1H, m), 3.00 (1H, dd, J=17Hz, 4Hz), 3.58 (1H, m), 3.84 (1H, m), 4.21 (1H, m), 4.24 (2H, m), 4.51 (1H, m), 4.58 (1H, m), 4.88 (1H, d, J=4Hz ), 4.98 ( 1H, J=9.5Hz ), 5.11 (6H, m), 5.52 (1H, d, J=7.5Hz), 6.24 (1H, d, J=9.5Hz ) , 7.3–7.4 (15H, m)

Step 2:

Preparation of 2-Benzyloxycarbonyl-1-(benzyloxycarbonylmethyl)ethyl 6-O-(3-Benzyloxycarbonyl-2R-tetradecanoylaminopropanoyl)-2-deoxy-3-O-tetradecanoyl-2-tetradecanoylamino-α-D-glucopyranoside The compound obtained in Step 1 above was reacted with tetradecanoic acid in the same manner as in Example 5, Step 2 to obtain the titled compound as a white waxy solid.

$[\alpha]_D^{25}$: +19.3° (c=0.6, chloroform) $^1$H-NMR (CDCl$_3$/TMS) δ: 0.88 (9H, t, J=7Hz), 1.25 (60H, br), 1.58 (6H, m), 2.09–2.19 (4H, m), 2.32 (2H, m), 2.60 (3H, m), 2.79 (1H, m), 2.89 (1H, dd, J=16Hz, 4Hz), 3.04 (1H, dd, J=16Hz, 5Hz ), 3.55 (1H, m), 3.84 (1H, m), 4.20 (1H, m), 4.25 (1H, m), 4.42 (1H, m), 4.53 (1H, dd, J=12Hz, 4Hz ), 4.83 (1H, m), 4.87 (1H, d, J=3.5Hz), 4.98 (1H, t, J=10Hz), 5.11 (6H, m), 6.23 (1H, d, J=9Hz), 6.44 (1H, d, J=8Hz), 7.3–7.4 (15H, m)

Step 3:

Preparation of 2-Carboxy-1-(carboxymethyl)-ethyl 6-O-(3-Carboxy-2R-tetradecanoylaminopropanoyl)-2-deoxy-3-O-tetradecanoyl-2-tetradecanoylamino-α-D-glucopyranoside (Compound No. 22)

The compound obtained in Step 2 above was reacted in the same manner as in Example 9, Step 3 to obtain the titled compound as a white powder.

$[\alpha]_D^{25}$: +46.1° (C=0.6, methanol) IR (KBr): 3360, 1740, 1180 cm$^{-1}$ $^1$H-NMR (CDCl$_3$—CD$_3$OD (1:1)/TMS ) δ: 0.90 (9H, t, J=7Hz), 1.29 (60H, br), 1.59 (6H, m), 2.20 (2H, m), 2.25 (2H, m), 2.31 (2H, m), 2.66 (3H, m), 2.74 (1H, dd, J=16Hz, 7Hz), 2.84 ( 1H, dd, J=17Hz, 7Hz ), 2.88 ( 1H, dd, J=17Hz, 5Hz), 3.59 (1H, t, J=10Hz), 3.96 (1H, dt, J=10Hz, 3Hz), 4.11 (1H, dd, J=11Hz, 3Hz), 4.34–4.46 (3H, m), 4.79 (1H, t, J=6Hz), 4.97 (1H, d, J=3Hz), 5.06 (1H, dd, J=11Hz, 9Hz)

EXAMPLE 23

Step 1:

Preparation of 2-Benzyloxycarbonyl-1-(benzyloxycarbonylmethyl)ethyl 6-O-{4-Benzyloxycarbonyl-2R-[6-(4-ethylphenyl)hexanoylamino]butanoyl}-2-deoxy-3-O-tetradecanoyl-2-tetradecanoylamino-α-D-glucopyranoside The compound obtained in Example 6, Step 1 was reacted with 6-(4-ethylphenyl)hexanoic acid in the same manner as in Example 5, Step 2 to obtain the titled compound as a colorless oily substance.

$[\alpha]_D^{25}$: +23.1° (c=0.5, chloroform) $^1$H-NMR (CDCl$_3$/TMS) δ: 0.88 ( 6H, t, J=7Hz), 1.25 (br), 1.60 (m), 2.0–2.7 (m), 2.80 (1H, dd, J=16Hz, 6.5Hz), 3.74 (1H, m), 3.88 (1H, m), 4.23 (2H, m), 4.41 (1H, m), 4.48 (1H, m), 4.52 (1H, m), 4.88 (1H, d, J=4Hz), 4.99 (1H, t, J=10Hz), 5.10 (6H, m), 6.25 (1H, d, J=9.5Hz), 6.37 (1H, d, J=7Hz), 7.1–7.4 (19H, m)

Step 2:

Preparation of 2-Carboxy-1-(carboxymethyl)ethyl 6-O-{4-Carboxy-2R-[6-(4-ethylphenyl)hexanoylamino]butanoyl}-2-deoxy-3-O-tetradecanoyl-2-tetradecanoylamino-α-D-glucopyranoside (Compound No. 23)

The compound obtained in Step 1 above was reacted in the same manner as in Example 7, Step 2 to obtain the titled compound as a white powder. The product had a vague melting point and turned brown at about 147° C.

$[\alpha]_D^{25}$: +44.3° (c=0.5, methanol ) IR (KBr): 3380, 1735, 1650, 1545 cm$^{-1}$ $^1$H-NMR (CDCl$_3$—CD$_3$OD (1:1)/TMS ) δ: 0.88 (6H, t), 1.27 (br), 1.60 (m), 2.0–2.35 (m), 2.43 (2H, t, J=7.5Hz), 2.55–2.67 (m) , 2.77 (1H, dd, J=16Hz, 6Hz), 3.63 (1H, t, J=9.5Hz), 3.97 (1H, m), 4.15 (1H, dd, J=11Hz, 3.5Hz), 4.37 (m), 4.43 (1H, m), 4.47 (1H, m), 4.96 (1H, d, J=3.5Hz), 5.07 (1H, t, J=10.5Hz), 7.09 (4H, s)

TEST EXAMPLE

Monocytes (5.0×10$^4$/well) isolated from a heparin-added blood sample (taken from a healthy person) by means of a specific gravity separatory liquid were used. Monocytes were cultured for 4 hours in a 10% fetal bovine serum-added RPMI-1640 medium (0.5 ml/well) to which 0, 1, 10 or 100 ng/ml of LPS (*E. coli* 0127:B8, DIFCO) and 0.5, 5 or 50 ng/ml of a test compound had been added. The TNF activity of the supernatant liquid of the culture was determined by a cytotoxic test against L929 cells. The results obtained are shown in Table 3 below.

TABLE 3

| Test Compound No. | Concn. of Test Compound (ng/ml) | Concn. of LPS (ng/ml) | TNF Activity (n = 3) (Mean ± Standard Deviation) (unit/ml) |
| --- | --- | --- | --- |
| none | — | 0 | <0.078 |
|  |  | 1 | 5.8 ± 1.5 |
|  |  | 10 | 7.5 ± 1.2 |
|  |  | 100 | 9.9 ± 1.9 |
| 1 | 0.5 | 0 | <0.078 |
|  |  | 1 | 1.9 ± 1.1 |
|  |  | 10 | 0.9 ± 0.1 |
|  |  | 100 | 2.5 ± 0.9 |
| 1 | 5 | 0 | <0.078 |
|  |  | 1 | 1.0 ± 0.2 |
|  |  | 10 | 0.8 ± 0.1 |
|  |  | 100 | 1.8 ± 0.9 |
| 1 | 50 | 0 | <0.078 |
|  |  | 1 | 1.6 ± 0.4 |
|  |  | 10 | 0.8 ± 0.4 |
|  |  | 100 | <0.078 |
| 2 | 0.5 | 0 | <0.078 |
|  |  | 1 | 0.8 ± 0.1 |
|  |  | 10 | 1.0 ± 0.3 |
|  |  | 100 | 1.4 ± 0.5 |
| 2 | 5 | 0 | <0.078 |
|  |  | 1 | 1.9 ± 0.3 |
|  |  | 10 | 1.4 ± 0.7 |
|  |  | 100 | 2.0 ± 0.3 |
| 2 | 50 | 0 | <0.078 |
|  |  | 1 | 0.8 ± 0.6 |
|  |  | 10 | 0.8 ± 0.5 |
|  |  | 100 | 1.4 ± 0.3 |

The results in Table 3 prove that the compounds according to the present invention significantly inhibit TNF derivation by endotoxin (LPS) at a very low level.

The compounds of the present invention are of low toxicity. For example, when each of Compound Nos. 1 to 3 was intravenously injected to the tail of mice, no abnormality was observed at a level of 200 μg/mice.

While the invention has been described in detail and with reference to specific examples thereof, it will be apparent to one skilled in the art that various changes and modifications can be made therein without departing from the spirit and scope thereof.

What is claimed is:

1. A compound represented by formula (I):

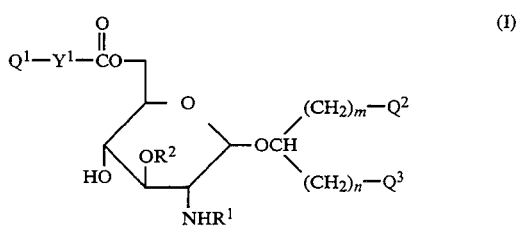

wherein R$^1$ represents —CO—Z$^1$—N(Z$^{11}$)—CO—Z$^2$—H or —CO—Z$^3$—H, wherein Z$^1$, Z$^2$, and Z$^3$ each represent an alkylene group having from 1 to 20 carbon atoms, a phenylene group, or a combination thereof, and Z$^{11}$ represents a hydrogen atom, an alkyl group having from 1 to 20 carbon atoms which may be substituted with a phenyl group, a phenyl group which may be substituted with an alkyl group having from 1 to 20 carbon atoms, or an alkylene group having from 1 to 20 carbon atoms which may contain therein a phenylene group; $R^2$ represents —CO—$Z^4$—N($Z^{12}$)—CO—$Z^5$—H, —CO—$Z^6$—H or a hydrogen atom, wherein $Z^4$, $Z^5$, and $Z^6$ each have the same meaning as $Z^1$, and $Z^{12}$ has the same meaning as $Z^{11}$; $Q^1$ and $Q^2$ each represent a carboxyl group or a phosphonoxy group; $Q^3$ represents a hydrogen atom, a carboxyl group or a phosphonoxy group; m represents 0 or an integer of from 1 to 20; n represents 0 or an integer of from 1 to 20; $Y^1$ represents an alkylene group having from 1 to 10 carbon atoms which may contain one or more substituents selected from —OCOR$^{11}$ and —NHCOR$^{12}$, wherein $R^{11}$ represents —$Z^{13}$ or —$Z^7$—N($Z^{14}$)—CO—$Z^8$—H, wherein $Z^7$ and $Z^8$ each have the same meaning as $Z^1$, and $Z^{13}$ and $Z^{14}$ each have the same meaning as $Z^{11}$, and $R^{12}$ represents —$Z^{15}$ or —$Z^9$—N($Z^{16}$)—CO—$Z^{10}$—H, wherein $Z^9$ and $Z^{10}$ each have the same meaning as $Z^1$, and $Z^{15}$ and $Z^{16}$ each have the same meaning as $Z^{11}$, or a salt thereof.

2. A compound as claimed in claim 1, wherein $Q^1$, $Q^2$, and $Q^3$ each represent a carboxyl group; $R^1$ repesents a tetradecanoyl group; $R^2$ represents an N-dodecanoylglycyl group; and m and n each represent 1.

3. A compound as claimed in claim 1, wherein $Q^1$, $Q^2$, and $Q^3$ each represent a carboxyl group; $R^1$ represents a tetradecanoyl group; $R^2$ represents an N-dodecanoylglycyl group; $Y^1$ represents a carboxyalkyl group having a tetradecanoyloxy group and/or a tetradecanoylamino group in the side chain thereof; and m and n each represent 1.

4. A compound as claimed in claim 1, wherein $Q^1$, $Q^2$, and $Q^3$ each represent a carboxyl group; $R^1$ represents a tetradecanoyl group; $R^2$ represents an N-dodecanoylglycyl group; $Y^1$ represents a phosphonoxyalkyl group having a tetradecanoyloxy group and/or a tetradecanoylamino group in the side chain thereof; and m and n each represent 1.

5. A compound as claimed in claim 1, wherein $Q^1$, $Q^2$, and $Q^3$ each represent a carboxyl group; $R^1$ represents a benzoylaminoalkyl group; $R^2$ represents an N-dodecanoylglycyl group; and m and n each represent 1.

6. A compound as claimed in claim 1, wherein $Q^1$, $Q^2$, and $Q^3$ each represent a carboxyl group; $R^1$ represents an N-dodecanoylsarcosyl group; $R^2$ represents an N-dodecanoylglycyl group; and m and n each represent 1.

7. A compound as claimed in claim 1, wherein $Q^1$ represents —COOH; $Q^2$ represents —OPO(OH)$_2$; $Q^3$ represents a hydrogen atom; $R^1$ and $R^2$ each represent a tetradecanoyl group; $Y^1$ represents an ethylene group having a tetradecanoyloxy group and/or a tetradecanoylamino group; m represents 1; and n represents 0.

8. A compound as claimed in claim 1, wherein $Q^1$ represents —COOH; $Q^2$ represents —OPO(OH)$_2$; $Q^3$ represents a hydrogen atom; $R^1$ and $R^2$ each represent a tetradecanoyl group; $Y^1$ represents a propylene group having a tetradecanoyloxy group and/or a tetradecanoylamino group; m represents 1; and n represents 0.

* * * * *